(12) United States Patent
Takata et al.

(10) Patent No.: US 10,464,943 B2
(45) Date of Patent: Nov. 5, 2019

(54) EPOXY COMPOUND, CURABLE COMPOSITION CONTAINING THE SAME, AND CURED PRODUCT OBTAINED BY CURING CURABLE COMPOSITION

(71) Applicant: JXTG NIPPON OIL & ENERGY CORPORATION, Tokyo (JP)

(72) Inventors: Shohei Takata, Tokyo-to (JP); Ryuichi Ueno, Tokyo-to (JP); Hisashi Sone, Tokyo-to (JP); Atsushi Kameyama, Tokyo-to (JP)

(73) Assignee: JXTG NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 16/308,110

(22) PCT Filed: Jun. 8, 2017

(86) PCT No.: PCT/JP2017/021246
§ 371 (c)(1),
(2) Date: Dec. 7, 2018

(87) PCT Pub. No.: WO2017/213206
PCT Pub. Date: Dec. 14, 2017

(65) Prior Publication Data
US 2019/0161494 A1 May 30, 2019

(30) Foreign Application Priority Data

Jun. 10, 2016 (JP) .................................. 2016-116591
Oct. 20, 2016 (JP) .................................. 2016-206395

(51) Int. Cl.
| | |
|---|---|
| *C07D 493/08* | (2006.01) |
| *C08G 59/24* | (2006.01) |
| *C08K 5/1515* | (2006.01) |
| *C08L 87/00* | (2006.01) |
| *C08K 5/00* | (2006.01) |
| *C08K 5/3445* | (2006.01) |
| *C08K 5/42* | (2006.01) |

(52) U.S. Cl.
CPC ........... *C07D 493/08* (2013.01); *C08G 59/24* (2013.01); *C08K 5/1515* (2013.01); *C08L 87/00* (2013.01); *C07B 2200/07* (2013.01); *C08K 5/0091* (2013.01); *C08K 5/3445* (2013.01); *C08K 5/42* (2013.01)

(58) Field of Classification Search
CPC .................................................... C07D 493/08
USPC ....................................................... 549/543
See application file for complete search history.

(56) References Cited

U.S. PATENT DOCUMENTS

2010/0249341 A1    9/2010  Sato et al.

FOREIGN PATENT DOCUMENTS

| JP | 49-126658 | 12/1974 |
|---|---|---|
| JP | 49126658 | * 12/1974 |
| JP | 2004-99445 | 4/2004 |
| JP | 2004-143362 | 5/2004 |
| JP | 2006-36665 | 2/2006 |
| JP | 2008-31424 | 2/2008 |

OTHER PUBLICATIONS

John McMurry, "Organic Chemistry", Fifth Edition, p. 143 (2000).
International Preliminary Report on Patentability dated Dec. 20, 2018 in International (PCT) Application No. PCT/JP2017/021246.
International Search Report dated Aug. 22, 2017 in International Application No. PCT/JP2017/021246.

* cited by examiner

*Primary Examiner* — Niloofar Rahmani
(74) *Attorney, Agent, or Firm* — Wenderoth, Lind & Ponack, L.L.P.

(57) ABSTRACT

The present invention discloses a composition comprising at least one or more stereoisomers of a compound represented by the following Formula (1), wherein, in a gas chromatogram obtained by analyzing the composition by gas chromatography, the ratio of the area of the maximum peak with respect to the total area of peaks derived from the stereoisomers is 60% or more; and wherein the maximum peak is present within the range of retention time of from 27.6 to 28.0 minutes. The present invention also discloses: a curable composition comprising the above described composition, and one selected from the group consisting of a thermal cationic polymerization initiator, an acid anhydride-based curing agent and a curing accelerator, and a photo-cationic polymerization initiator; as well as a cured product therefrom. The above described curable composition is useful in that it allows for the production of a cured product having a high heat resistance.

(1)

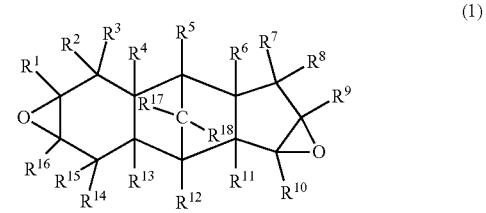

(In the Formula (1), $R^1$ to $R^{18}$ are each independently selected from the group consisting of a hydrogen atom, an alkyl group and an alkoxy group.)

23 Claims, 7 Drawing Sheets

EPOXY COMPOUND, CURABLE COMPOSITION CONTAINING THE SAME, AND CURED PRODUCT OBTAINED BY CURING CURABLE COMPOSITION

CROSS-REFERENCE TO RELATED APPLICATIONS

The present patent application is based upon and claims the benefit of priority from previously filed Japanese Patent Application No. 2016-116591 (filed on Jun. 10, 2016), and Japanese Patent Application No. 2016-206395 (filed on Oct. 20, 2016). The entire disclosures of the above described patent applications are incorporated herein by reference.

BACKGROUND OF THE INVENTION

Field of the Invention

The present invention relates to an epoxy compound, a curable composition containing the same, and a cured product obtained from curing the curable composition.

Background Art

Curable compositions containing epoxy compounds are used as materials for surface protective films for semiconductor devices and organic thin film elements (such as organic electro-luminescent elements and organic thin film solar cell elements), interlayer insulators, protective insulating films for printed alignment substrates, and fiber-reinforced composite materials and the like. Among these epoxy compounds, epoxy compounds containing an aromatic ring have been used as compounds which allow for the production of cured products having an excellent heat resistance and the like.

However, compounds containing an aromatic ring generally have a high dielectric constant due to having a high electron density, and accordingly, in the applications as described above, there has been a problem for use in the field of electronic materials. Further, these compounds are also associated with a problem that coloration and the like thereof lead to a reduction in the light transmittance of the resulting resin. In view of the above, alicyclic diamine compounds having no aromatic ring are drawing attention, in recent years. In addition, curable compositions for use in the applications as described above are required to be able to produce cured products having a high moisture resistance and heat resistance.

Among epoxy compounds, epoxy compounds having an alicyclic skeleton are known as compounds which allow for the production of cured products having an excellent heat resistance and the like. For example, Patent Document 1 discloses an epoxy compound which has an alicyclic skeleton with a specific structure and which allows for the production of a resin having an excellent heat resistance and the like.

Further, among these epoxy compounds, epoxy compounds having two or more alicyclic skeletons within the molecule are known as compounds which allow for the production of cured products having an excellent heat resistance, transparency and the like. For example, Patent Document 2 discloses a curable composition containing dicyclopentadiene diepoxide or tricyclopentadiene diepoxide. In addition, Patent Document 3 discloses a curable composition containing a diepoxybicyclohexyl compound. However, the epoxy compounds having alicyclic skeletons which are proposed in Patent Documents 2 and 3 have room for a further improvement, from the viewpoint of improving the heat resistance of the resulting cured products and avoiding decreasing the weight reduction upon curing.

PRIOR ART DOCUMENTS

Patent Documents

Patent Document 1: JP S49-126658 A
Patent Document 2: JP 2004-143362 A
Patent Document 3: JP 2008-31424 A

SUMMARY OF THE INVENTION

Problems to be Solved by the Invention

The present inventors have found out that the heat resistance of cured products obtained by curing the curable compositions disclosed in Patent Documents 2 and 3, and the like are not yet sufficient, and there is room for a further improvement.

Further, the present inventors have found out that, in a composition of an epoxy compound comprising one or more stereoisomers having a specific structure, it is possible to dramatically improve the heat resistance of a cured product obtained by curing a curable composition containing the above described composition, by adjusting the ratio of a peak area(s) derived from a stereoisomer(s) having a specific retention time with respect to the total area of peaks derived from the stereoisomers contained in the composition to equal to or more than a specific numerical value. In addition, the present inventors have clarified the specific steric structure of the stereoisomer corresponding to the maximum peak.

The present invention has been made based on the above findings, and an object of the invention is to provide a composition, or an epoxy compound having a specific stereoisomeric structure, which allows for producing a cured product having a markedly improved heat resistance.

Means for Solving the Problems

In other words, the present invention encompasses the following inventions.

[1] A composition comprising at least one or more stereoisomers of a compound represented by the following Formula (1):

[Chem. 1]

(1)

(wherein $R^1$ to $R^{18}$ are each independently selected from the group consisting of a hydrogen atom, an alkyl group and an alkoxy group)

wherein, in a gas chromatogram obtained by analyzing the composition by gas chromatography under the following analysis conditions, the ratio of the area of the maximum peak with respect to the total area of peaks derived from the stereoisomers is 60% or more, wherein the maximum peak is present within the range of retention time of from 27.6 to 28.0 minutes, and wherein the analysis conditions are as follows:

column: HP-1 (manufactured by Agilent Technologies Inc.), length: 60.0 m, inner diameter: 250 μm, film thickness: 0.25 μm;

liquid phase: 100% dimethylpolysiloxane;

carrier gas: $N_2$;

flow velocity: 1.3 mL/min;

sample inlet temperature: 140° C.;

detector temperature: 250° C.;

sample injection volume: 0.2 μL; and temperature increase conditions: 80° C. (3 min), 80 to 150° C. (10° C./min), 150 to 250° C. (5° C./min), 250° C. (20 min).

[2] A composition comprising at least one or more stereoisomers of a compound represented by the following Formula (1):

[Chem. 2]

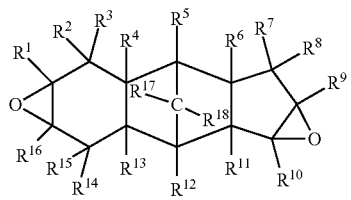

(1)

(wherein $R^1$ to $R^{18}$ are each independently selected from the group consisting of a hydrogen atom, an alkyl group and an alkoxy group)

wherein, in a gas chromatogram obtained by analyzing the composition by gas chromatography under the following analysis conditions, the ratio of the area of the maximum peak within the range of retention time of from 27.6 to 28.0 minutes with respect to the total area of peaks within the range of retention time of from 27.5 to 29.0 minutes is 60% or more, and wherein the analysis conditions are as follows:

column: HP-1 (manufactured by Agilent Technologies Inc.), length: 60.0 m, inner diameter: 250 μm, film thickness: 0.25 μm;

liquid phase: 100% dimethylpolysiloxane;

carrier gas: $N_2$;

flow velocity: 1.3 mL/min;

sample inlet temperature: 140° C.;

detector temperature: 250° C.;

sample injection volume: 0.2 μL; and temperature increase conditions: 80° C. (3 min), 80 to 150° C. (10° C./min), 150 to 250° C. (5° C./min), 250° C. (20 min).

[3] The composition according to [1] or [2], wherein the compound represented by the Formula (1) is a reaction product of a compound represented by the following Formula (2):

[Chem. 3]

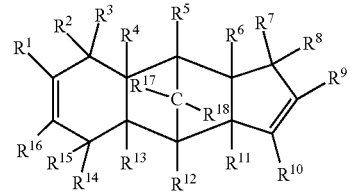

(2)

(wherein $R^1$ to $R^{18}$ are each independently selected from the group consisting of a hydrogen atom, an alkyl group and an alkoxy group)

with a peracid.

[4] The composition according to any one of [1] to [3], wherein the maximum peak is the first peak among the peaks derived from the stereoisomers.

[5] The composition according to any one of [1] to [3], wherein the maximum peak is the first peak appearing after a retention time of 27.5 minutes, among the peaks within the range of retention time of from 27.5 to 29.0 minutes.

[6] The composition according to any one of [1] to [5], wherein the $R^1$ to $R^{18}$ are all hydrogen atoms.

[7] The composition according to any one of [1] to [6], wherein the stereoisomer corresponding to the maximum peak is represented by the following Formula (3):

[Chem. 4]

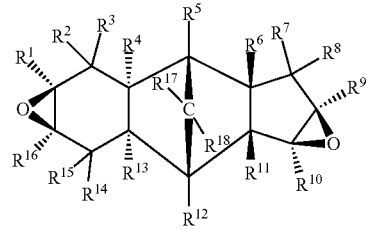

(3)

(wherein $R^1$ to $R^{18}$ are each independently selected from the group consisting of a hydrogen atom, an alkyl group and an alkoxy group).

[8] An epoxy compound represented by the following Formula (3):

[Chem. 5]

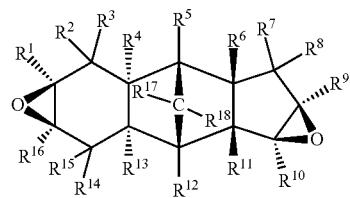

(3)

(wherein $R^1$ to $R^{18}$ are each independently selected from the group consisting of a hydrogen atom, an alkyl group and an alkoxy group).

[9] A curable composition comprising:

the composition according to any one of [1] to [7] or the epoxy compound according to [8]; and one selected from the group consisting of: a thermal cationic polymerization initiator, an acid anhydride-based curing agent and a curing accelerator, and a photo-cationic polymerization initiator.

[10] The curable composition according to [9], further comprising one kind, or two or more kinds selected from the group consisting of an epoxy compound other than the compound represented by the Formula (1), an oxetane compound and a vinyl ether.

[11] The curable composition according to [9] or [10], wherein the thermal cationic polymerization initiator is selected from the group consisting of aromatic sulfonium salt-based thermal cationic polymerization initiators, aromatic iodonium salt-based thermal cationic polymerization initiators and aluminum complex-based thermal cationic polymerization initiators.

[12] The curable composition according to [11], wherein the thermal cationic polymerization initiator is an aromatic sulfonium salt-based thermal cationic polymerization initiator.

[13] The curable composition according to any one of [10] to [12], wherein, in cases where the curable composition does not include any of the epoxy compound other than the compound represented by the Formula (1), the oxetane compound and the vinyl ether, the content of the thermal cationic polymerization initiator is from 0.1 to 15 parts by mass with respect to 100 parts by mass of the composition according to any one of [1] to [7] or the epoxy compound according to [8] contained in the curable composition; and in cases where the curable composition includes one kind, or two or more kinds selected from the group consisting of the epoxy compound other than the compound represented by the Formula (1), the oxetane compound and the vinyl ether, the content of the thermal cationic polymerization initiator is from 0.1 to 15 parts by mass with respect to 100 parts by mass of the total amount of the composition according to any one of [1] to [7] or the epoxy compound according to [8], the epoxy compound other than the compound represented by the Formula (1), the oxetane compound and the vinyl ether, which are contained in the curable composition.

[14] The curable composition according to [10], wherein, in cases where the curable composition does not include the epoxy compound other than the compound represented by the Formula (1), the content of the acid anhydride-based curing agent is from 0.6 to 1.2 equivalents with respect to one epoxy equivalent of the composition according to any one of [1] to [7] or the epoxy compound according to [8] contained in the curable composition; and in cases where the curable composition includes the epoxy compound other than the compound represented by the Formula (1), the content of the acid anhydride-based curing agent is from 0.6 to 1.2 equivalents with respect to one epoxy equivalent of a mixture of epoxy compounds composed of the composition according to any one of [1] to [7] or the epoxy compound according to [8] and the epoxy compound other than the compound represented by the Formula (1), which are contained in the curable composition.

[15] The curable composition according to [10] or [14], wherein, in cases where the curable composition does not include the epoxy compound other than the compound represented by the Formula (1), the content of the curing accelerator is from 0.1 to 10 parts by mass with respect to 100 parts by mass of the composition according to any one of [1] to [7] or the epoxy compound according to [8] contained in the curable composition; and in cases where the curable composition includes the epoxy compound other than the compound represented by the Formula (1), the content of the curing accelerator is from 0.1 to 10 parts by mass with respect to 100 parts by mass of the total amount of the composition according to any one of [1] to [7] or the epoxy compound according to [8] and the epoxy compound other than the compound represented by the Formula (1), which are contained in the curable composition.

[16] The curable composition according to [9], [14] or [15], wherein the curing accelerator is an imidazole-based curing accelerator.

[17] The curable composition according to any one of [11] to [16], wherein the content of the composition according to any one of [1] to [7] or the epoxy compound according to [8] is from 10 to 99% by mass.

[18] The curable composition according to [9] or [10], wherein the photo-cationic polymerization initiator is an aromatic sulfonium salt-based photo-cationic polymerization initiator.

[19] The curable composition according to [10] or [18], wherein, in cases where the curable composition does not include any of the epoxy compound other than the compound represented by the Formula (1), the oxetane compound and the vinyl ether, the content of the photo-cationic polymerization initiator is from 0.1 to 20 parts by mass with respect to 100 parts by mass of the composition according to any one of [1] to [7] or the epoxy compound according to [8] contained in the curable composition; and in cases where the curable composition includes one kind, or two or more kinds selected from the group consisting of the epoxy compound other than the compound represented by the Formula (1), the oxetane compound and the vinyl ether, the content of the photo-cationic polymerization initiator is from 0.1 to 20 parts by mass with respect to 100 parts by mass of the total amount of the composition according to any one of [1] to [7] or the epoxy compound according to [8], the epoxy compound other than the compound represented by the Formula (1), the oxetane compound and the vinyl ether, which are contained in the curable composition.

[20] The curable composition according to [18] or [19], wherein the content of the composition according to any one of [1] to [7] or the epoxy compound according to [8] is from 1 to 50% by mass.

[21] The curable composition according to any one of [10] to [20], wherein the epoxy compound other than the compound represented by the Formula (1) is selected from the group consisting of glycidyl ether-type epoxides, glycidyl ester-type epoxides and alicyclic epoxides.

[22] A method of producing a cured product, the method comprising the step of curing the curable composition according to any one of [9] to [21].

[23] A cured product from the curable composition according to any one of [9] to [21].

Effect of the Invention

The present invention provides a composition or an epoxy compound which allows for the production of a cured product having a high heat resistance.

DETAILED DESCRIPTION OF THE INVENTION

1. Definitions

Figure 1:
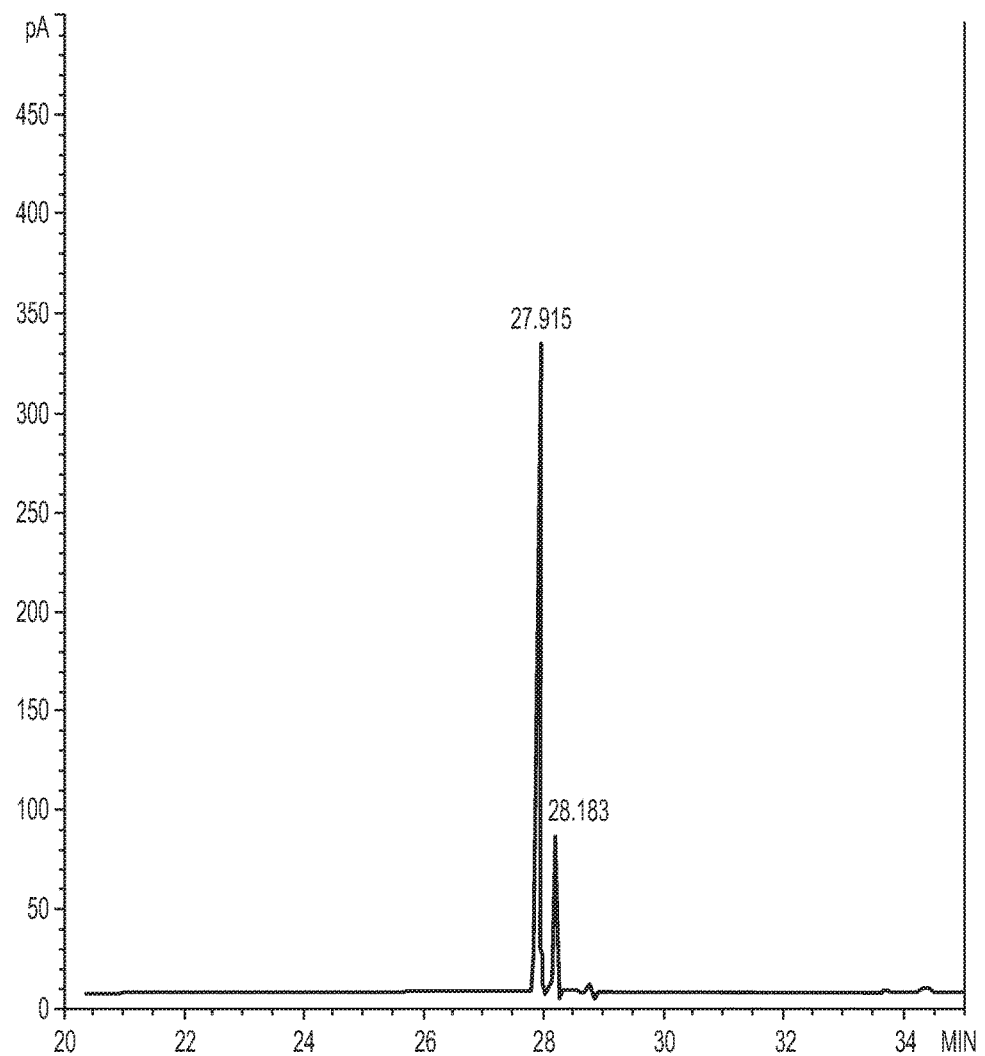
FIG. 1 shows a gas chromatograph of a composition (A-1) prepared in Preparation Example 1.

In the present specification, the terms "part(s)", "%" and the like used to describe the composition are represented on a mass basis, unless otherwise specified.

In the present specification, the term "epoxy equivalent" is defined by the mass of an epoxy compound containing one equivalent of epoxy groups. In the case of a mixture composed of m kinds (wherein m is an integer of 2 or more) of epoxy compounds, the epoxy equivalent of the mixture is represented by the following equation:

[Math 1]

Epoxy equivalent of a mixture of epoxy compounds =

$$\frac{\sum_{n=1}^{n} \text{Mass of epoxy compound } n}{\sum_{n=1}^{n} \frac{\text{Mass of epoxy compound } n}{\text{Epoxy equivalent of epoxy compound } n}}$$

The epoxy equivalent of an epoxy compound can be measured in accordance with JIS K7236.

2. Composition Comprising Stereoisomers of Epoxy Compound

The composition according to the present invention is a composition comprising at least one or more stereoisomers of a compound represented by the following Formula (1), wherein, in a gas chromatogram obtained by analyzing the composition by gas chromatography under the following analysis conditions, the ratio of the area of the maximum peak with respect to the total area of peaks derived from the stereoisomers is 60% or more, and wherein the maximum peak is present within the range of retention time of from 27.6 to 28.0 minutes. Further, the composition according to the present invention is a composition comprising at least one or more stereoisomers of a compound represented by the following Formula (1), wherein, in a gas chromatogram obtained by analyzing the composition by gas chromatography under the following analysis conditions, the ratio of the area of the maximum peak within the range of retention time of from 27.6 to 28.0 minutes with respect to the total area of peaks within the range of retention time of from 27.5 to 29.0 minutes is 60% or more.

[Chem. 6]

(1)

(In the Formula (1), $R^1$ to $R^{18}$ are each independently selected from the group consisting of a hydrogen atom, an alkyl group and an alkoxy group.)

(Analysis Conditions)
Column: HP-1 (manufactured by Agilent Technologies Inc.), length: 60.0 m, inner diameter: 250 μm, film thickness: 0.25 μm
Liquid phase: 100% dimethylpolysiloxane
Carrier gas: $N_2$
Flow velocity: 1.3 mL/min
Sample inlet temperature: 140° C.
Detector temperature: 250° C.
Sample injection volume: 0.2 μL
Temperature increase conditions: 80° C. (3 min), 80 to 150° C. (10° C./min), 150 to 250° C. (5° C./min), 250° C. (20 min The composition according to the present invention comprises at least one or more stereoisomers of a compound represented by the Formula (1).

The epoxy compound according to the present invention is characterized in that it is represented by the following Formula (3):

[Chem. 7]

(3)

(wherein $R^1$ to $R^{18}$ are each independently selected from the group consisting of a hydrogen atom, an alkyl group and an alkoxy group).

In the composition according to the present invention or the epoxy compound according to the present invention, $R^1$ to $R^{18}$ in the above described Formula (1) or the above described Formula (3) are each independently selected from the group consisting of a hydrogen atom, an alkyl group and an alkoxy group. Among these, $R^1$ to $R^{18}$ are particularly preferably hydrogen atoms. The alkyl group preferably has from 1 to 10 carbon atoms, and more preferably from 1 to 5 carbon atoms. Further, the alkyl group may be a linear alkyl group or a branched alkyl group. The alkoxy group preferably has from 1 to 10 carbon atoms, and more preferably from 1 to 5 carbon atoms. It is particularly preferred that $R^1$ to $R^{18}$ be all hydrogen atoms.

In the case of a curable composition containing the composition according to the present invention or the epoxy compound according to the present invention and a thermal cationic polymerization initiator, or alternatively, in the case of a curable composition containing the composition according to the present invention or the epoxy compound according to the present invention, an acid anhydride-based curing agent and a curing accelerator, the composition according to the present invention or the epoxy compound according to the present invention contained in the curable composition preferably has an epoxy equivalent of from 85 to 600 g/eq, more preferably from 90 to 600 g/eq, still more preferably from 85 to 300 g/eq, still more preferably from 90 to 300 g/eq, and yet still more preferably from 90 to 200 g/eq. The curable composition according to the present invention may further contain any of other compounds to be described later. However, the content of the composition according to the present invention or the epoxy compound according to the present invention contained in the curable composition according to the present invention is preferably from 10 to 99% by mass, more preferably from 10 to 80% by mass, still more preferably from 15 to 99% by mass, and yet still more preferably from 15 to 60% by mass, from the viewpoint of improving heat resistance of the resulting cured product and/or preventing a reduction in weight upon curing.

In the case of a curable composition containing the composition according to the present invention or the epoxy compound according to the present invention and a photo-cationic polymerization initiator, the composition according to the present invention or the epoxy compound according to the present invention contained in the curable composition preferably has an epoxy equivalent of from 85 to 600 g/eq, more preferably from 85 to 300 g/eq, and still more preferably from 85 to 200 g/eq. The curable composition according to the present invention may further contain any of other compounds to be described later. However, the content of the composition according to the present invention or the epoxy compound according to the present invention contained in the curable composition according to the present invention is preferably from 1 to 50% by mass, and more preferably from 5 to 40% by mass, from the viewpoint of improving the heat resistance the resulting cured product.

In the gas chromatogram obtained by analyzing the composition according to the present invention by gas chromatography under the above described analysis conditions, the ratio of the area of the maximum peak with respect to the total area of peaks derived from the stereoisomers of the compound represented by the above described Formula (1) which are contained in the composition is 60% or more. The ratio is preferably 62% or more, 70% or more, 80% or more, 84% or more, 91% or more, or 96% or more. Further, the maximum peak is present within the range of retention time of from 27.6 to 28.0 minutes.

In the gas chromatogram obtained by analyzing the composition according to the present invention by gas chromatography under the above described analysis conditions, the ratio of the area of the maximum peak within the range of retention time of from 27.6 to 28.0 minutes with respect to the total area of peaks within the range of retention time of from 27.5 to 29.0 minutes is 60% or more. The ratio is preferably 62% or more, 70% or more, 80% or more, 84% or more, 91% or more, or 96% or more.

In the composition according to the present invention, the stereoisomer corresponding to the maximum peak is preferably represented by the following Formula (3):

[Chem. 8]

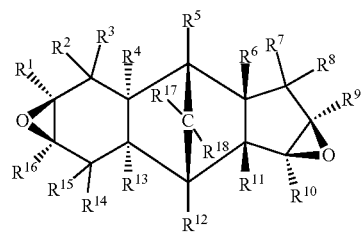

(3)

(wherein $R^1$ to $R^{18}$ are each independently selected from the group consisting of a hydrogen atom, an alkyl group and an alkoxy group).

$R^1$ to $R^{18}$ in the Formula (3) are the same as defined in the above described Formula (1).

As shown in the following conditions, the column to be used in a chromatography analysis is composed of dimethylsiloxane. For example, it is possible to use Agilent 19091Z-436E, manufactured by Agilent Technologies Inc., or the like (Analysis Conditions)
Measurement apparatus: Agilent 6850 series, manufactured by Agilent Technologies Inc.
Column: HP-1 (manufactured by Agilent Technologies Inc.), length: 60.0 m, inner diameter: 250 μm, film thickness: 0.25 μm
Liquid phase: 100% dimethylpolysiloxane
Carrier gas: $N_2$
Flow velocity: 1.3 mL/min
Sample inlet temperature: 140° C.
Detector temperature: 250° C.
Sample injection volume: 0.2 μL
Temperature increase conditions: 80° C. (3 min), 80 to 150° C. (10° C./min), 150 to 250° C. (5° C./min), 250° C. (20 min)

The maximum peak in the composition according to the present invention preferably appears first of all the peaks derived from the stereoisomers contained in the composition. More specifically, the maximum peak is preferably a peak which appears first within the retention time of from 27.5 to 30.0 minutes.

Further, the maximum peak in the composition according to the present invention is preferably the first peak appearing after a retention time of 27.5 minutes, among the peaks within the range of retention time of from 27.5 to 29.0 minutes.

In the composition according to the present invention, it is preferred that $R^1$ to $R^{18}$ in the above described Formula (1) be all hydrogen atoms.

In the present invention, the compound represented by the Formula (1) is preferably a reaction product of a compound represented by the following Formula (2):

[Chem. 9]

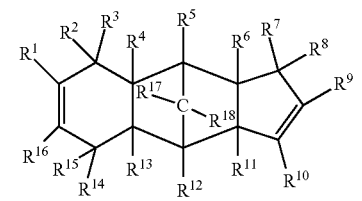

(2)

(wherein $R^1$ to $R^{18}$ are each independently selected from the group consisting of a hydrogen atom, an alkyl group and an alkoxy group)
with a peracid.

$R^1$ to $R^{18}$ in the Formula (2) are the same as defined in the above described Formula (1).

In one embodiment, the compound represented by the Formula (1) can be synthesized by allowing the compound represented by the Formula (2) to react with a peracid, such as hydrogen peroxide, peracetic acid or perbenzoic acid.

In one embodiment, the compound satisfying the Formula (2) can be synthesized by the Diels-Alder reaction of cyclopentadiene and dicyclopentadiene.

In the composition according to the present invention, it is possible to increase the ratio of the area of the maximum peak present within the range of retention time of from 27.6 to 28.0 minutes, by further carrying out purification by crystallization. More specifically, the ratio of the area of the maximum peak can be increased by: dissolving the epoxy compound in isopropyl alcohol; cooling the resulting solution to room temperature (25° C.) to allow crystallization to occur; filtering the resultant to obtain solids, and washing the resulting solids with isopropyl alcohol, followed by drying.

In the composition according to the present invention, it is possible to increase the ratio of the area of the maximum peak within the range of retention time of from 27.6 to 28.0 minutes by further carrying out purification by crystallization, in the gas chromatogram obtained by analyzing the composition by gas chromatography under the above described analysis conditions. More specifically, the ratio of the area of the maximum peak can be increased by: dissolving the epoxy compound in isopropyl alcohol; cooling the resulting solution to room temperature (25° C.) to allow crystallization to occur; filtering the resultant to obtain solids, and washing the resulting solids with isopropyl alcohol, followed by drying.

3. Curable Composition

The curable composition according to the present invention is characterized in that it comprises: the composition according to the present invention or the epoxy compound according to the present invention; and one selected from the group consisting of: a thermal cationic polymerization initiator, an acid anhydride-based curing agent and a curing accelerator, and a photo-cationic polymerization initiator.

(1) Thermal Cationic Polymerization Initiator

Examples of cationic polymerization initiators which can be contained in the curable composition according to the present invention include thermal cationic polymerization initiators (initiators capable of generating cationic active species by the application of thermal energy thereto) and photo-cationic polymerization initiators (initiators capable of generating cationic active species by the irradiation of light or an electron beam thereto). The combined use of the composition according to the present invention or the epoxy compound according to the present invention with a thermal cationic polymerization initiator enables to improve the heat resistance of the resulting cured product to an even higher level, as well as to decrease the reduction in the weight thereof which occurs upon curing. The above combination also enables to improve the transparency of the resulting cured product.

The thermal cationic polymerization initiator may be, for example: (i) an aromatic sulfonium salt-based thermal cationic polymerization initiator; (ii) a phosphonium salt-based thermal cationic polymerization initiator; (iii) a quaternary ammonium salt-based thermal cationic polymerization initiator; (iv) an aluminum complex-based thermal cationic polymerization initiator; (v) an aromatic iodonium salt-based thermal cationic polymerization initiator; (vi) an aromatic diazonium salt-based thermal cationic polymerization initiator; or (vii) a pyridinium-based thermal cationic polymerization initiator.

Examples of the aromatic sulfonium salt-based thermal cationic polymerization initiator include: hexafluoroantimonate salts such as
(2-ethoxy-1-methyl-2-oxoethyl)methyl-2-naphthalenylsulfonium hexafluoroantimonate, 4-(methoxycarbonyloxy)phenylbenzylmethylsulfonium hexafluoroantimonate, 4-acetoxyphenyldimethylsulfonium hexafluoroantimonate, 4-hydroxyphenylbenzylmethylsulfonium hexafluoroantimonate, 4-hydroxyphenyl(o-methylbenzyl)methylsulfonium hexafluoroantimonate, 4-hydroxyphenyl(α-naphthylmethyl)methylsulfonium hexafluoroantimonate, diphenyl-4-(phenylthio)phenylsulfonium hexafluoroantimonate, triphenylsulfonium hexafluoroantimonate, bis[4-(di(4-(2-hydroxyethoxy))phenylsulfonio)phenyl]sulfide bishexafluoroantimonate, and bis[4-(diphenylsulfonio)phenyl]sulfide bishexafluoroantimonate; hexafluorophosphate salts such as (2-ethoxy-1-methyl-2-oxoethyl)methyl-2-naphthalenylsulfonium hexafluorophosphate, 4-acetoxyphenylbenzylmethylsulfonium hexafluorophosphate, 4-hydroxyphenyl(o-methylbenzyl)methylsulfonium hexafluorophosphate, 4-hydroxyphenyl(α-naphthylmethyl)methylsulfonium hexafluorophosphate, diphenyl-4-(phenylthio)phenylsulfonium hexafluorophosphate, triphenylsulfonium hexafluorophosphate, bis[4-(di(4-(2-hydroxyethoxy))phenylsulfonio)phenyl]sulfide bishexafluorophosphate, and bis[4-(diphenylsulfonio)phenyl]sulfide bishexafluorophosphate; hexafluoroarsenate salts such as 4-hydroxyphenyl(o-methylbenzyl)methylsulfonium hexafluoroarsenate, and 4-hydroxyphenylbenzylmethylsulfonium hexafluoroarsenate; tetrafluoroborate salts such as (2-ethoxy-1-methyl-2-oxoethyl)methyl-2-naphthalenylsulfonium tetrafluoroborate, 4-hydroxyphenyl(o-methylbenzyl)methylsulfonium tetrafluoroborate, 4-hydroxyphenylbenzylmethylsulfonium tetrafluoroborate, diphenyl-4-(phenylthio)phenylsulfonium tetrafluoroborate, triphenylsulfonium tetrafluoroborate, bis[4-(di(4-(2-hydroxyethoxy))phenylsulfonio)phenyl]sulfide bistetrafluoroborate, and bis[4-(diphenylsulfonio)phenyl]sulfide bistetrafluoroborate; trifluoromethanesulfonate salts such as 4-hydroxyphenyl(o-methylbenzyl)methylsulfonium trifluoromethanesulfonate, and 4-hydroxyphenylbenzylmethylsulfonium trifluoromethanesulfonate; trifluoromethanesulfonate salts such as diphenyl-4-(phenylthio)phenylsulfonium trifluoromethanesulfonate; bis(trifluoromethanesulfone)imide salts such as 4-hydroxyphenyl(α-naphthylmethyl)methylsulfonium bis(trifluoromethanesulfone)imide, and 4-hydroxyphenylbenzylmethylsulfonium bis(trifluoromethanesulfone)imide; tetrakis(pentafluorophenyl)borate salts such as (2-ethoxy-1-methyl-2-oxoethyl)methyl-2-naphthalenylsulfonium tetrakis(pentafluorophenyl)borate, 4-(methoxycarbonyloxy)phenylbenzylmethylsulfonium tetrakis(pentafluorophenyl)borate, 4-hydroxyphenyl(o-methylbenzyl)methylsulfonium tetrakis(pentafluorophenyl)borate, 4-hydroxyphenyl(α-naphthylmethyl)methylsulfonium tetrakis(pentafluorophenyl)borate, 4-hydroxyphenylbenzylmethylsulfonium tetrakis(pentafluorophenyl)borate, diphenyl-4-(phenylthio)phenylsulfonium tetrakis(pentafluorophenyl)borate, triphenylsulfonium tetrakis(pentafluorophenyl)borate, bis

[4-(di(4-(2-hydroxyethoxy))phenylsulfonio)phenyl]sulfide tetrakis(pentafluorophenyl)borate, and bis[4-(diphenylsulfonio)phenyl]sulfide tetrakis(pentafluorophenyl)borate.

Examples of (ii) the phosphonium salt-based thermal cationic polymerization initiator include ethyltriphenylphosphonium hexafluoroantimonate, and tetrabutylphosphonium hexafluoroantimonate.

Examples of (iii) the quaternary ammonium salt-based thermal cationic polymerization initiator include N,N-dimethyl-N-benzylanilinium hexafluoroantimonate, N,N-diethyl-N-benzylanilinium tetrafluoroborate, N,N-dimethyl-N-benzylpyridinium hexafluoroantimonate, N,N-diethyl-N-benzylpyridinium trifluoromethanesulfonic acid, N,N-dimethyl-N-(4-methoxybenzyl)pyridinium hexafluoroantimonate, N,N-diethyl-N-(4-methoxybenzyl)pyridinium hexafluoroantimonate, N,N-diethyl-N-(4-methoxybenzyl)toluidinium hexafluoroantimonate, and N,N-dimethyl-N-(4-methoxybenzyl)toluidinium hexafluoroantimonate.

Examples of (iv) the aluminum complex-based thermal cationic polymerization initiator include aluminum carboxylates; aluminum alkoxide, aluminium chloride, aluminum (alkoxide) acetoacetic acid chelate, acetoacetonato aluminum, and ethylacetoacetato aluminum.

Examples of (v) the aromatic iodonium salt-based thermal cationic polymerization initiator include phenyliodonium hexafluorophosphate, diphenyliodonium hexafluoroantimonate, diphenyliodonium tetrafluoroborate, diphenyliodonium tetrakis(pentafluorophenyl)borate, diphenyliodonium hexafluorophosphate, diphenyliodonium trifluoromethanesulfonate, bis(dodecylphenyl)iodonium hexafluorophosphate, bis(dodecylphenyl)iodonium hexafluoroantimonate, bis(dodecylphenyl)iodonium tetrafluoroborate, bis(dodecylphenyl)iodonium tetrakis(pentafluorophenyl)borate, 4-methylphenyl-4-(1-methylethyl)phenyliodonium hexafluorophosphate, 4-methylphenyl-4-(1-methylethyl)phenyliodonium hexafluoroantimonate, 4-methylphenyl-4-(1-methylethyl)phenyliodonium tetrafluoroborate, and 4-methylphenyl-4-(1-methylethyl)phenyliodonium tetrakis(pentafluorophenyl)borate.

Examples of (vi) the aromatic diazonium salt-based thermal cationic polymerization initiator include phenyldiazonium hexafluorophosphate, phenyldiazonium hexafluoroantimonate, phenyldiazonium tetrafluoroborate and phenyldiazonium tetrakis(pentafluorophenyl)borate.

Examples of (vii) the pyridinium-based thermal cationic polymerization initiator include 1-benzyl-2-cyanopyridinium hexafluorophosphate, 1-benzyl-2-cyanopyridinium hexafluoroantimonate, 1-benzyl-2-cyanopyridinium tetrafluoroborate, 1-benzyl-2-cyanopyridinium tetrakis(pentafluorophenyl)borate, 1-(naphthylmethyl)-2-cyanopyridinium hexafluorophosphate, 1-(naphthylmethyl)-2-cyanopyridinium hexafluoroantimonate, 1-(naphthylmethyl)-2-cyanopyridinium tetrafluoroborate, and 1-(naphthylmethyl)-2-cyanopyridinium tetrakis(pentafluorophenyl)borate.

These thermal cationic polymerization initiators may be used alone, or as a mixture of two or more kinds thereof.

Among these, an aromatic sulfonium salt-based thermal cationic polymerization initiator is more preferred, and a monoaryl-based thermal cationic polymerization initiator, such as 4-acetoxyphenyldimethylsulfonium hexafluoroantimonate, is particularly preferred. The combined use of any of these specific thermal cationic polymerization initiators with the composition according to the present invention or the epoxy compound according to the present invention enables to improve the heat resistance of the resulting cured product to an even higher level, as well as to further decrease the reduction in the weight thereof which occurs upon curing. The above combination also enables to improve the transparency of the resulting cured product.

In cases where the curable composition according to the present invention does not contain any of an epoxy compound other than the compound represented by the Formula (1) to be described later, an oxetane compound to be described later and a vinyl ether to be described later, the content of the thermal cationic polymerization initiator in the curable composition is preferably from 0.1 to 15 parts by mass, and more preferably from 0.3 to 7 parts by mass with respect to 100 parts by mass of the composition according to the present invention or the epoxy compound according to the present invention contained in the curable composition. Further, in cases where the curable composition contains one kind, or two or more kinds selected from the group consisting of the epoxy compound other than the compound represented by the Formula (1), the oxetane compound and the vinyl ether, the content of the thermal cationic polymerization initiator in the curable composition is preferably from 0.1 to 15 parts by mass, and more preferably from 0.3 to 7 parts by mass with respect to 100 parts by mass of the total amount of the composition according to the present invention or the epoxy compound according to the present invention, the epoxy compound other than the compound represented by the Formula (1), the oxetane compound and the vinyl ether, which are contained in the curable composition. When the content of the thermal cationic polymerization initiator is adjusted within the above described numerical range, the heat resistance of the resulting cured product can be improved to an even higher level. Further, the weight reduction of the cured product upon curing can further be decreased. In addition, the transparency of the cured product can be further improved.

The thermal cationic polymerization initiator to be contained in the curable composition according to the present invention is more preferably selected from the group consisting of aromatic sulfonium salt-based thermal cationic polymerization initiators, aromatic iodonium salt-based thermal cationic polymerization initiators and aluminum complex-based thermal cationic polymerization initiators. Further, the thermal cationic polymerization initiator to be contained in the curable composition according to the present invention is still more preferably an aromatic sulfonium salt-based thermal cationic polymerization initiator.

(2) Acid Anhydride-based Curing Agent

Examples of the acid anhydride-based curing agent to be contained in the curable composition according to the present invention include hexahydrophthalic anhydride, methylhexahydrophthalic anhydride, tetrahydrophthalic anhydride, methyltetrahydrophthalic anhydride, endomethylenetetrahydrophthalic anhydride, methylnadic anhydride, methylbutenyltetrahydrophthalic anhydride, hydrogenated methylnadic anhydride, trialkyltetrahydrophthalic anhydride, cyclohexanetricarboxylic anhydride, methylcyclohexenedicarboxylic anhydride, methylcyclohexanetetracarboxylic acid dianhydride, maleic anhydride, phthalic anhydride, succinic anhydride, dodecenylsuccinic anhydride, octenylsuccinic anhydride, pyromellitic anhydride, trimellitic anhydride, alkylstyrene-maleic anhydride copolymer, chlorendic anhydride, polyazelaic anhydride, benzophenone tetracarboxylic anhydride, ethylene glycol bisanhydrotrimellitate, glycerol tristrimellitate, glycerin bis(anhydrotrimellitate) monoacetate, benzophenonetetracarboxylic acid, polyadipic anhydride, polysebacic anhydride, poly(ethyloctadecanedioic acid) anhydride, poly(phenylhexadecanedioic acid) anhydride, HET anhydride, and norbornane-2,3-dicarboxylic anhydride.

Among these, hexahydrophthalic anhydride and methylhexahydrophthalic anhydride are preferred, because the combined use of any of these with the composition according to the present invention or the epoxy compound according to the present invention allows for improving the heat resistance and the transparency of the resulting cured product to an even higher level. The curable composition according to the present invention can contain one kind, or two or more kinds of the acid anhydride-based curing agents described above.

From the viewpoint of improving the heat resistance of the resulting cured product, the content of the acid anhydride-based curing agent in the curable composition according to the present invention, in cases where the curable composition does not contain the epoxy compound other than the compound represented by the Formula (1) to be described later, is preferably from 0.5 to 1.5 equivalents, more preferably from 0.6 to 1.2 equivalents, and still more preferably from 0.8 to 1.2 equivalents with respect to one epoxy equivalent of the composition according to the present invention or the epoxy compound according to the present invention contained in the curable composition. Further, in cases where the curable composition according to the present invention contains the epoxy compound other than the compound represented by the Formula (1), the content of the acid anhydride-based curing agent in the curable composition is preferably from 0.5 to 1.5 equivalents, more preferably from 0.6 to 1.2 equivalents, and still more preferably from 0.8 to 1.2 equivalents with respect to one epoxy equivalent of a mixture of epoxy compounds composed of the composition according to the present invention or the epoxy compound according to the present invention and the epoxy compound other than the compound represented by the Formula (1), which are contained in the curable composition.

(3) Curing Agent Other than Acid Anhydride-based Curing Agent

Examples of the curing agent which can be contained in the curable composition according to the present invention include, in addition to the acid anhydride-based curing agents, amine-based curing agents, phenol-based curing agents and latent curing agents.

Examples of the amine-based curing agent include polyoxyethylene diamine, polyoxypropylene diamine, polyoxybutylene diamine, polyoxypentylene diamine, polyoxyethylene triamine, polyoxypropylene triamine, polyoxybutylene triamine, polyoxypentylene triamine, diethylene triamine, triethylene tetramine, tetraethylene pentamine, m-xylene diamine, trimethylhexamethylene diamine, 2-methylpentamethylene diamine, diethylaminopropylamine, isophorone diamine, 1,3-bisaminomethylcyclohexane, bis(4-aminocyclohexyl)methane, norbornane diamine, 1,2-diaminocyclohexane, diaminodiphenylmethane, metaphenylene diamine, diaminodiphenyl sulfone, and N-aminoethylpiperazine.

Examples of the phenol-based curing agent include xylylene skeleton-containing phenol novolac resins, dicyclopentadiene skeleton-containing phenol novolac resins, biphenyl skeleton-containing phenol novolac resins, fluorene skeleton-containing phenol novolac resins, terpene skeleton-containing phenol novolac resins, bisphenol A novolac, bisphenol F novolac, bisphenol S novolac, bisphenol AP novolac, bisphenol C novolac, bisphenol E novolac, bisphenol Z novolac, biphenol novolac, tetramethyl bisphenol A novolac, dimethyl bisphenol A novolac, tetramethyl bisphenol F novolac, dimethyl bisphenol F novolac, tetramethyl bisphenol S novolac, dimethyl bisphenol S novolac, tetramethyl-4,4'-biphenol novolac, trishydroxyphenylmethane novolac, resorcinol novolac, hydroquinone novolac, pyrogallol novolac, diisopropylidene novolac, 1,1-di-4-hydroxyphenylfluorene novolac, phenolated polybutadiene novolac, phenol novolac, cresol novolac, ethylphenol novolac, butylphenol novolac, octylphenol novolac, and naphthol novolac.

Examples of the latent curing agent include dicyandiamide, adipic acid dihydrazide, sebacic acid dihydrazide, dodecanedioic acid dihydrazide, isophthalic acid dihydrazide, ketimines, imidazole compounds, dihydrazide compounds, amine adduct-based latent curing agents. The curable composition according to the present invention may contain one kind, or two or more kinds of the curing agents as described above.

In a preferred embodiment of the curable composition according to the present invention, the curing agent is one or more curing agents selected from the group consisting of acid anhydride-based curing agents, amine-based curing agents, phenol-based curing agents and latent curing agents.

(4) Curing Accelerator

Examples of the curing accelerator to be contained in the curable composition according to the present invention include: phosphines and quaternary salts thereof, such as triphenylphosphine, triphenylbenzylphosphonium tetraphenylborate, tetrabutylphosphonium diethylphosphorodithioate, tetraphenylphosphonium bromide, tetrabutylphosphonium acetate, tetra-n-butylphosphonium bromide, tetra-n-butylphosphonium benzotriazolate, tetra-n-butylphosphonium tetrafluoroborate, tetra-n-butylphosphonium tetraphenylborate, methyltriphenylphosphonium bromide, ethyltriphenylphosphonium bromide, ethyltriphenylphosphonium iodide, ethyltriphenylphosphonium acetate, methyltri-n-butylphosphonium dimethylphosphate, n-butyltriphenylphosphonium bromide, benzyltriphenylphosphonium chloride, and tetraphenylphosphonium tetraphenylborate; imidazoles such as 2-ethyl-4-methylimidazole, 1,2-dimethylimidazole, 1-benzyl-2-phenylimidazole, 2-methylimidazole, 2-phenylimidazole, 1-(2-cyanoethyl)-2-ethyl-4-methylimidazole, 2,4-diamino-6-[2-methylimidazolyl-(1)]ethyl-s-triazine, 2-phenylimidazoline, and 2,3-dihydro-1H-pyrrolo[1,2-a]benzimidazole; tertiary amines and quaternary salts thereof such as, tris(dimethylaminomethyl)phenol, benzyldimethylamine, and tetrabutylammonium bromide; super strong basic organic compounds such as 1,8-diazabicyclo(5,4,0)undecene-7 and 1,5-diazabicyclo(4,3,0)nonene-5; organic metal carboxylates such as zinc octylate, zinc laurate, zinc stearate, and tin octylate; metal-organic chelate compounds such as benzoylacetone zinc chelate, dibenzoylmethane zinc chelate and ethyl acetoacetate zinc chelate; and tetra-n-butylsulfonium-o,o-diethyl phosphorodithionate.

Among these, an imidazole-based curing accelerator is particularly preferred, because the combined use thereof with the composition according to the present invention or the epoxy compound according to the present invention allows for improving the heat resistance of the resulting cured product to an even higher level.

The curable composition according to the present invention may contain one kind, or two or more kinds of the curing accelerators as described above.

From the viewpoint of improving the heat resistance of the resulting cured product, the content of the curing accelerator in the curable composition according to the present invention, in cases where the curable composition does not contain the epoxy compound other than the compound represented by the Formula (1) to be described later, is preferably from 0.1 to 10 parts by mass, more preferably from 0.2 to 8 parts by mass, and still more preferably from 0.5 to 6 parts by mass with respect to 100 parts by mass of the composition according to the present invention or the epoxy compound according to the present invention contained in the curable composition. Further, in cases where the curable composition according to the present invention contains the epoxy compound other than the compound represented by the Formula (1), the content of the curing accelerator in the curable composition is preferably from 0.1 to 10 parts by mass, more preferably from 0.2 to 8 parts by mass, and still more preferably from 0.5 to 6 parts by mass with respect to 100 parts by mass of the total amount of the composition according to the present invention or the epoxy compound according to the present invention and the epoxy compound other than the compound represented by the Formula (1), which are contained in the curable composition.

(5) Photo-cationic Polymerization Initiator

The photo-cationic polymerization initiator to be contained in the curable composition according to the present invention is one which generates cationic species or Lewis acid when irradiated with an active energy ray such as a visible ray, UV light, an X ray or an electron beam, thereby initiating a polymerization reaction of a cationically polymerizable compound. As the photo-cationic polymerization initiator to be contained in the curable composition according to the present invention, it is possible to use, for example, a compound such as an onium salt, a metallocene complex, or an iron-allene complex. Examples of the onium salt which can be used include aromatic sulfonium salts, aromatic iodonium salts, aromatic diazonium salts, aromatic phosphonium salts and aromatic selenium salts. As the counter ions for these salts, anions such as $CF_3SO_3^-$, $BF_4^-$, $PF_6^-$, $AsF_6^-$, and $SbF_6^-$ are used. Among these, it is more preferred to use an aromatic sulfonium salt-based photo-cationic polymerization initiator, since it exhibits an excellent curing performance due to having UV absorption properties even in the wavelength range of 300 nm or more, and allows for providing a cured product having a good mechanical strength and adhesion strength. The curable composition according to the present invention may contain two or more kinds of the photo-cationic polymerization initiators.

Examples of the aromatic sulfonium salt include diphenyl-4-(phenylthio)phenylsulfonium hexafluorophosphate, 4,4'-bis(diphenylsulfonio)diphenylsulfide bishexafluorophosphate, 4,4'-bis[di(β-hydroxyethoxy)phenylsulfonio]diphenylsulfide bishexafluoroantimonate, 4,4'-bis[di(β-hydroxyethoxy)phenylsulfonio]diphenylsulfide bishexafluorophosphate, 7-[di(p-toluyl)sulfonio]-2-isopropylthioxanthone hexafluoroantimonate, 7-[di(p-toluyl)sulfonio]-2-isopropylthioxanthone tetrakis(pentafluorophenyl)borate, 4-phenylcarbonyl-4'-diphenylsulfonio-diphenylsulfide hexafluorophosphate, 4-(p-tert-butylphenylcarbonyl)-4'-diphenylsulfonio-diphenylsulfide hexafluoroantimonate, 4-(p-tert-butylphenylcarbonyl)-4'-di(p-toluyl)sulfonio-diphenylsulfide tetrakis(pentafluorophenyl)borate, diphenyl-4-(phenylthio)phenylsulfonium hexafluoroantimonate, triphenylsulfonium trifluoromethanesulfonate, bis[4-(diphenylsulfonio)phenyl]sulfide bishexafluoroantimonate, and (4-methoxyphenyl)diphenylsulfonium hexafluoroantimonate.

Examples of the aromatic iodonium salt include diphenyliodonium tetrakis(pentafluorophenyl)borate, diphenyliodonium hexafluorophosphate, diphenyliodonium hexafluoroantimonate, di(4-nonylphenyl)iodonium hexafluorophosphate, (4-methoxyphenyl)phenyliodonium hexafluoroantimonate, and bis(4-t-butylphenyl)iodonium hexafluorophosphate.

Examples of the aromatic diazonium salt include benzenediazonium hexafluoroantimonate, benzenediazonium hexafluorophosphate, benzenediazonium tetrafluoroborate, and 4-chlorobenzenediazonium hexafluorophosphate.

Examples of the aromatic phosphonium salt include benzyltriphenylphosphonium hexafluoroantimonate.

Examples of the aromatic selenium salt include triphenylselenium hexafluorophosphate.

Examples of the iron-allene complex include xylene-cyclopentadienyl iron (II) hexafluoroantimonate, cumene-cyclopentadienyl iron (II) hexafluorophosphate, and xylene-cyclopentadienyl iron (II) tris(trifluoromethylsulfonyl)methanide.

In cases where the curable composition according to the present invention does not contain any of the epoxy compound other than the compound represented by the Formula (1) to be described later, the oxetane compound to be described later, and the vinyl ether to be described later, the content of the photo-cationic polymerization initiator in the curable composition is preferably from 0.1 to 20 parts by mass, and more preferably from 0.3 to 15 parts by mass with respect to 100 parts by mass of the composition according to the present invention or the epoxy compound according to the present invention contained in the curable composition. Further, in cases where the curable composition according to the present invention contains one kind, or two or more kinds selected from the group consisting of the epoxy compound other than the compound represented by the Formula (1), the oxetane compound and the vinyl ether, the content of the photo-cationic polymerization initiator in the curable composition is preferably from 0.1 to 20 parts by mass, and more preferably from 0.3 to 15 parts by mass with respect to 100 parts by mass of the total amount of the composition according to the present invention or the epoxy compound according to the present invention, the epoxy compound other than the compound represented by the Formula (1), the oxetane compound and the vinyl ether, which are contained in the curable composition. When the content of the photo-cationic polymerization initiator is adjusted within the above described numerical range, the heat resistance of the resulting cured product can be improved to an even higher level. In addition, the transparency of the cured product can further be improved.

(6) Epoxy Compound Other than Compound Represented by the Formula (1)

The curable composition according to the present invention may contain an epoxy compound other than the compound represented by the Formula (1) (in the present specification, sometimes also referred to as "the other epoxy compound"), depending on the application. Examples of the epoxy compound other than the compound represented by the Formula (1) include glycidyl ether-type epoxides, glycidyl ester-type epoxides, glycidyl amine-type epoxides and alicyclic epoxides; as well as oligomers and polymers thereof.

Examples of the glycidyl ether-type epoxide include: glycidyl ethers of divalent phenols such as bisphenol A diglycidyl ether, bisphenol F diglycidyl ether, bisphenol S diglycidyl ether, tetramethyl biphenol diglycidyl ether, hydrogenated bisphenol A diglycidyl ether, and brominated bisphenol A diglycidyl ether; glycidyl ethers of polyvalent phenols such as dihydroxynaphthyl cresol triglycidyl ether, tris(hydroxyphenyl)methane triglycidyl ether, tetrakis(hydroxyphenyl)ethane tetraglycidyl ether, dinaphthyltriol triglycidyl ether, phenol novolac glycidyl ether, cresol novolac glycidyl ether, xylylene skeleton-containing phenol novolac glycidyl ethers, dicyclopentadiene skeleton-containing phenol novolac glycidyl ethers, biphenyl skeleton-containing phenol novolac glycidyl ethers, terpene skeleton-containing phenol novolac glycidyl ethers, bisphenol A novolac glycidyl ether, bisphenol F novolac glycidyl ether, bisphenol S novolac glycidyl ether, bisphenol AP novolac glycidyl ether, bisphenol C novolac glycidyl ether, bisphenol E novolac glycidyl ether, bisphenol Z novolac glycidyl ether, biphenol novolac glycidyl ether, tetramethyl bisphenol A novolac glycidyl ether, dimethyl bisphenol A novolac glycidyl ether, tetramethyl bisphenol F novolac glycidyl ether, dimethyl bisphenol F novolac glycidyl ether, tetramethyl bisphenol S novolac glycidyl ether, dimethyl bisphenol S novolac glycidyl ether, tetramethyl-4,4'-biphenol novolac glycidyl ether, trishydroxyphenylmethane novolac glycidyl ether, resorcinol novolac glycidyl ether, hydroquinone novolac glycidyl ether, pyrogallol novolac glycidyl ether, diisopropylidene novolac glycidyl ether, 1,1-di-4-hydroxyphenylfluorene novolac glycidyl ether, phenolated polybutadiene novolac glycidyl ether, ethylphenol novolac glycidyl ether, butylphenol novolac glycidyl ether, octylphenol novolac glycidyl ether, naphthol novolac glycidyl ether, and hydrogenated phenol novolac glycidyl ether; glycidyl ethers of divalent alcohols such as ethylene glycol diglycidyl ether, propylene glycol diglycidyl ether, tetramethylene glycol diglycidyl ether, 1,6-hexanediol diglycidyl ether, cyclohexanedimethylol diglycidyl ether, polyethylene glycol diglycidyl ether, and polypropylene glycol diglycidyl ether; glycidyl ethers of polyols such as trimethylolpropane triglycidyl ether, glycerin triglycidyl ether, pentaerythritol tetraglycidyl ether, sorbitol hexaglycidyl ether, and polyglycerin polyglycidyl ether; and triglycidyl isocyanurate.

Examples of the glycidyl ester-type epoxide include: glycidyl esters of carboxylic acids such as glycidyl methacrylate, phthalic acid diglycidyl ester, isophthalic acid diglycidyl ester, terephthalic acid diglycidyl ester, cyclohexanedicarboxylic acid diglycidyl ester, and trimellitic acid triglycidyl ester; and glycidyl ester-type polyepoxides.

Examples of the glycidyl amine-type epoxide include: glycidyl aromatic amines such as N,N-diglycidylaniline, N,N-diglycidyltoluidine, N,N,N',N'-tetraglycidyldiaminodiphenylmethane, N,N,N',N'-tetraglycidyldiaminodiphenylsulfone, and N,N,N',N'-tetraglycidyldiethyldiphenylmethane; and glycidyl heterocyclic amines such as bis(N,N-diglycidylaminocyclohexyl)methane (hydride of N,N,N',N'-tetraglycidyldiaminodiphenylmethane), N,N,N',N'-tetraglycidyl-1,3-(bisaminomethyl)cyclohexane (hydride of N,N,N',N'-tetraglycidylxylylene diamine), trisglycidylmelamine, triglycidyl-p-aminophenol, N-glycidyl-4-glycidyloxypyrrolidone.

Examples of the alicyclic epoxide include vinyl cyclohexene dioxide, limonene dioxide, dicyclopentadiene dioxide, bis(2,3-epoxycyclopentyl) ether, ethylene glycol bisepoxy dicyclopentyl ether, 3,4-epoxy-6-methylcyclohexylmethyl 3',4'-epoxy-6'-methylcyclohexane carboxylate, 3,4-epoxycyclohexylmethyl 3,4-epoxycyclohexane carboxylate, 3,4-epoxy-1-methylcyclohexyl 3,4-epoxy-1-methylhexane carboxylate, 3,4-epoxy-3-methylcyclohexylmethyl 3,4-epoxy-3-methylhexane carboxylate, 3,4-epoxy-5-methylcyclohexylmethyl 3,4-epoxy-5-methylcyclohexane carboxylate, 2-(3,4-epoxycyclohexyl-5,5-spiro-3,4-epoxy)cyclohexane-metadioxane, methylenebis(3,4-epoxycyclohexane), (3,3',4,4'-diepoxy)bicyclohexyl, 1,2-epoxy-(2-oxiranyl)cyclohexane adduct of 2,2-bis (hydroxymethyl)-1-butanol, and tetrahydroindene diepoxide. The curable composition according to the present invention may contain one kind, or two or more kinds of epoxy compounds other than the compound represented by the Formula (1), such as those as described above.

The content of the above described epoxy compound other than the compound represented by the Formula (1) is preferably from 1 to 90% by mass, and more preferably from 5 to 85% by mass with respect to the amount of curable composition, from the viewpoint of improving the heat resistance of the resulting cured product.

In one preferred embodiment, the epoxy compound other than the compound represented by the Formula (1), which is contained in the curable composition according to the present invention, is selected from the group consisting of glycidyl ether-type epoxies, glycidyl ester-type epoxies and alicyclic epoxies.

(7) Reactive Diluent

The curable composition according to the present invention may further contain a reactive diluent in order to reduce the viscosity. Examples of the reactive diluent include a monoepoxy compound produced by the method described in Preparation Example 6, butyl glycidyl ether, 2-ethylhexyl glycidyl ether, glycidyl ether of a mixture of C12 and C13 alcohols, and 1,2-epoxy-4-vinylcyclohexane. The curable composition may contain one kind, or two or more kinds of the reactive diluents as described above. The mixing ratio of the reactive diluent may be adjusted as appropriate such that the curable composition containing the reactive diluent has a desired viscosity.

(8) Oxetane Compound

The curable composition according to the present invention may contain an oxetane compound. Examples of the oxetane compound include 1,4-bis[(3-ethyl-3-oxetanylmethoxy)methyl]benzene, 3-ethyl-3-hydroxymethyloxetane, 3-ethyl-3-(phenoxymethyl)oxetane, di[(3-ethyl-3-oxetanyl)methyl] ether, 3-ethyl-3-(2-ethylhexyloxymethyl)oxetane, 3-ethyl-3-(cyclohexyloxymethyl)oxetane, phenol novolac oxetane, 1,3-bis[(3-ethyloxetan-3-yl)]methoxybenzene, oxetanyl silsesquioxane, oxetanyl silicate, bis[1-ethyl (3-oxetanyl)]methyl ether, 4,4'-bis[(3-ethyl-3-oxetanyl) methoxymethyl]biphenyl, 4,4'-bis(3-ethyl-3-oxetanylmethoxy)biphenyl, ethylene glycol (3-ethyl-3-oxetanylmethyl) ether, diethylene glycol bis(3-ethyl-3-oxetanylmethyl) ether, bis(3-ethyl-3-oxetanylmethyl) diphenoate, trimethylolpropane propane tris(3-ethyl-3-oxetanylmethyl) ether, pentaerythritol tetrakis(3-ethyl-3-oxetanylmethyl) ether, and phenol novolac-type oxetane compounds. The curable composition according to the present invention may contain one kind, or two or more kinds of the oxetane compounds as described above.

The content of the oxetane compound in the curable composition according to the present invention is preferably from 1 to 90% by mass, and more preferably from 5 to 85% by mass, from the viewpoint of improving the heat resistance of the resulting cured product.

(9) Vinyl Ether Compound

The curable composition according to the present invention may contain a vinyl ether compound. Examples of the vinyl ether compound include: monofunctional vinyl ethers such as methyl vinyl ether, ethyl vinyl ether, propyl vinyl ether, and butyl vinyl ether; polyfunctional vinyl ethers such as ethylene glycol divinyl ether, butanediol divinyl ether, cyclohexanedimethanol divinyl ether, cyclohexanediol divinyl ether, trimethylolpropane trivinyl ether, pentaerythritol tetravinyl ether, glycerol trivinyl ether, triethylene glycol divinyl ether, and diethylene glycol divinyl ether; vinyl ether compounds containing a hydroxyl group such as hydroxyethyl vinyl ether, hydroxybutyl vinyl ether, cyclohexanedimethanol monovinyl ether, cyclohexanediol monovinyl ether, 9-hydroxynonyl vinyl ether, propylene glycol monovinyl ether, neopentyl glycol monovinyl ether, glycerol divinyl ether, glycerol monovinyl ether, trimethylolpropane divinyl ether, trimethylolpropane monovinyl ether, pentaerythritol monovinyl ether, pentaerythritol divinyl ether, pentaerythritol trivinyl ether, diethylene glycol monovinyl ether, triethylene glycol monovinyl ether, tetraethylene glycol monovinyl ether, tricyclodecanediol monovinyl ether, and tricyclodecane dimethanol monovinyl ether; and vinyl ethers containing different types of functional groups, such as 2-(2-vinyloxyethoxy)ethyl acrylate, and 2-(2-vinyloxyethoxy)ethyl methacrylate. The curable composition according to the present invention may contain one kind, or two or more kinds of the vinyl ether compounds as described above.

The content of the vinyl ether compound in the curable composition according to the present invention is preferably from 1 to 90% by mass, and more preferably from 5 to 85% by mass, from the viewpoint of improving the heat resistance of the resulting cured product.

(10) Compound Containing Hydroxyl Group

The curable composition according to the present invention may further contain a compound containing a hydroxyl group. Incorporation of a compound containing a hydroxyl group into the curable composition allows a moderate curing reaction to proceed. Examples of the compound containing a hydroxyl group include ethylene glycol, diethylene glycol, and glycerin. The curable composition according to the present invention may contain one kind, or two or more kinds of the compounds containing a hydroxyl group, such as those described above.

The content of the compound containing a hydroxyl group in the curable composition according to the present invention is preferably from 0.1 to 10% by mass, and more preferably from 0.2 to 8% by mass, from the viewpoint of improving the heat resistance of the resulting cured product.

(11) Other Components

The curable composition according to the present invention may further contain a solvent. Examples of the solvent include methyl ethyl ketone, ethyl acetate, toluene, methanol, and ethanol.

The curable composition according to the present invention may contain various types of additives to the extent that the properties of the composition are not impaired. Examples of the additives include fillers, silane coupling agents, mold release agents, coloring agents, flame retardants, antioxidants, photostabilizers and plasticizers, antifoaming agents, photostabilizers, coloring agents such as pigments and dyes, plasticizers, pH adjusting agents, coloration inhibitors, matting agents, deodorants, weather resistant agents, antistatic agents, yarn friction reducing agents, slip agents, and ion exchangers.

(12) Production of Curable Composition

The curable composition according to the present invention can be produced in accordance with technical common knowledge widely known to those skilled in the art, and the method of producing the curable composition and the components to be further included in the curable composition can be selected as appropriate.

4. Cured Product (1) Conditions for Curing

The cured product according to the present invention is obtained by curing the above described curable composition according to the present invention. The method of curing the curable composition is not particularly limited, and the composition can be cured by heating or irradiation of light, as appropriate.

In cases where the curable composition is cured by heating, the heating of the curable composition is preferably carried out in multiple stages, taking into consideration the degree of reactivity of the epoxy compound. This allows for a sufficient curing reaction to proceed. For example, the curing reaction can be carried out by performing a first heating at a temperature of from 100 to 130° C. for 10 to 150 minutes, a second heating at 140 to 160° C. for 10 to 150 minutes, a third heating at 170 to 200° C. for 60 to 180 minutes, and a fourth heating at 210 to 250° C. for 10 to 150 minutes. Alternatively, the curing reaction can also be carried out, for example, by performing a first heating at a temperature of from 100 to 130° C. for 10 to 150 minutes, a second heating at 140 to 200° C. for 10 to 150 minutes, and a third heating at 210 to 250° C. for 10 to 150 minutes. Still alternatively, the curing reaction can also be carried out, for example, by performing a first heating at a temperature of from 80 to 100° C. for 10 to 150 minutes, a second heating at 110 to 120° C. for 10 to 150 minutes, a third heating at 130 to 140° C. for 60 to 180 minutes, a fourth heating at 150 to 170° C. for 10 to 150 minutes, a fifth heating at 180 to 200° C. for 60 to 180 minutes and a sixth heating at 210 to 230° C. for 60 to 240 minutes. Still alternatively, the curing reaction can be carried out, for example, by performing a first heating at a temperature of from 100 to 110° C. for 10 to 150 minutes, a second heating at 120 to 150° C. for 10 to 150 minutes, a third heating at 160 to 220° C. for 10 to 150 minutes, and a fourth heating at 230 to 250° C. for 10 to 150 minutes. However, the heating conditions are not limited to those described above, and the heating is preferably carried out varying the conditions as appropriate, in view of the content of the epoxy compound and the properties of other compounds and the like contained in the curable composition.

In cases where the curable composition is cured by the irradiation of an active energy ray, such as a visible ray, UV light, an X ray or an electron beam, the type of the active energy ray used and the conditions for irradiation are preferably selected as appropriate, depending on the composition of the curable composition. In one embodiment, it is preferred that the irradiation of UV light be carried out such that the accumulated amount of light, which is represented as the product of the irradiation intensity and the irradiation time, is adjusted within the range of from 10 to 5,000 mJ/cm$^2$. When the accumulated amount of light irradiated to the curable composition is adjusted within the above described numerical range, it is possible to allow active species derived from the photo-cationic polymerization initiator to be generated sufficiently. This also allows for an improvement in the productivity.

(2) Applications of Cured Product

Specific examples of the application of the curable composition according to the present invention and the cured product obtained therefrom include: coating materials for coating on substrates such as metals, resin films, glass, paper and wood, surface protective films for semiconductor devices and organic thin film elements (for example, organic electroluminescent elements and organic thin film solar cell elements), hard coating agents, anti-fouling films and anti-reflection films; adhesive agents, tacky materials; various types of optical members such as lenses, prisms, filters, image display materials, lens arrays, sealing materials and reflector materials for optical semiconductor devices, sealing materials for semiconductor devices, optical waveguides, light guide plates, light diffusion plates, diffraction elements and optical adhesive agents; and materials such as casting materials, interlayer insulators, insulating films for printed alignment substrates and fiber-reinforced composite materials.

EXAMPLES

The present invention will now be described in further detail by way of Examples. However, the present invention is in no way limited by these Examples.

1. Preparation Example 1: Preparation of Composition (A-1)

Into a reaction vessel equipped with a thermometer, an agitator, a reflux tube and a dropping device, 559 g of a diolefin compound represented by the following Formula (4), 840 g of toluene, and 25 g of sodium acetate were charged. To the reactor, 1,219 g of a 38% aqueous solution of peracetic acid was added dropwise over eight hours, while stirring at room temperature. The stirring was continued at room temperature for 17 hours, followed by stirring at 30° C. for two hours.

[Chem. 10]

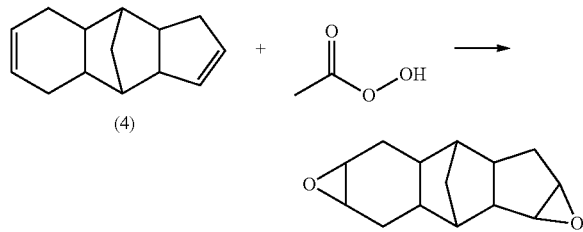

Subsequently, a 10% aqueous solution of sodium sulfite, a 20% aqueous solution of NaOH, and water were used to carry out washing. The resulting solution was concentrated with a rotary evaporator. Thereafter, the resultant was dissolved in isopropyl alcohol while heating at 63° C., and then cooled to −10° C. to allow crystallization to occur, followed by collecting solids by filtration. The solids collected by filtration were washed with 150 mL of isopropyl alcohol, and then dried to obtain 394 g of a composition (A-1) as white solids.

The resulting composition (A-1) was analyzed by gas chromatography under the following analysis conditions. FIG. 1 shows a gas chromatograph of the composition (A-1). As shown in FIG. 1, peaks derived from the stereoisomers of the compound represented by Formula (1) were observed within the range of retention time of from 27.5 to 29.0 minutes. As shown in FIG. 1, the ratio of the area of the maximum peak within the range of retention time of from 27.6 to 28.0 minutes with respect to the total area of peaks within the range of retention time of from 27.5 to 29.0 minutes was 84%.

(Analysis Conditions)
Measurement apparatus: Agilent 6850 series, manufactured by Agilent Technologies Inc.
Column: HP-1 (manufactured by Agilent Technologies Inc.), dimethylpolysiloxane, length: 60.0 m, inner diameter: 250 μm, film thickness: 0.25 μm
Carrier gas: $N_2$
Flow velocity: 1.3 mL/min
Sample inlet temperature: 140° C.
Detector temperature: 250° C.
Sample injection volume: 0.2 μL
Temperature increase conditions: 80° C. (3 min), 80 to 150° C. (10° C./min), 150 to 250° C. (5° C./min), 250° C. (20 min)

2. Preparation Example 2: Preparation of Composition (A-2)

A quantity of 10.0 g of the composition (A-1) was dissolved in isopropyl alcohol at 60° C., and cooled to 25° C. to allow crystallization to occur, followed by collecting solids by filtration. The solids collected by filtration were washed with 15 mL of isopropyl alcohol, and then dried to obtain 6.63 g of a composition (A-2).

Figure 2:
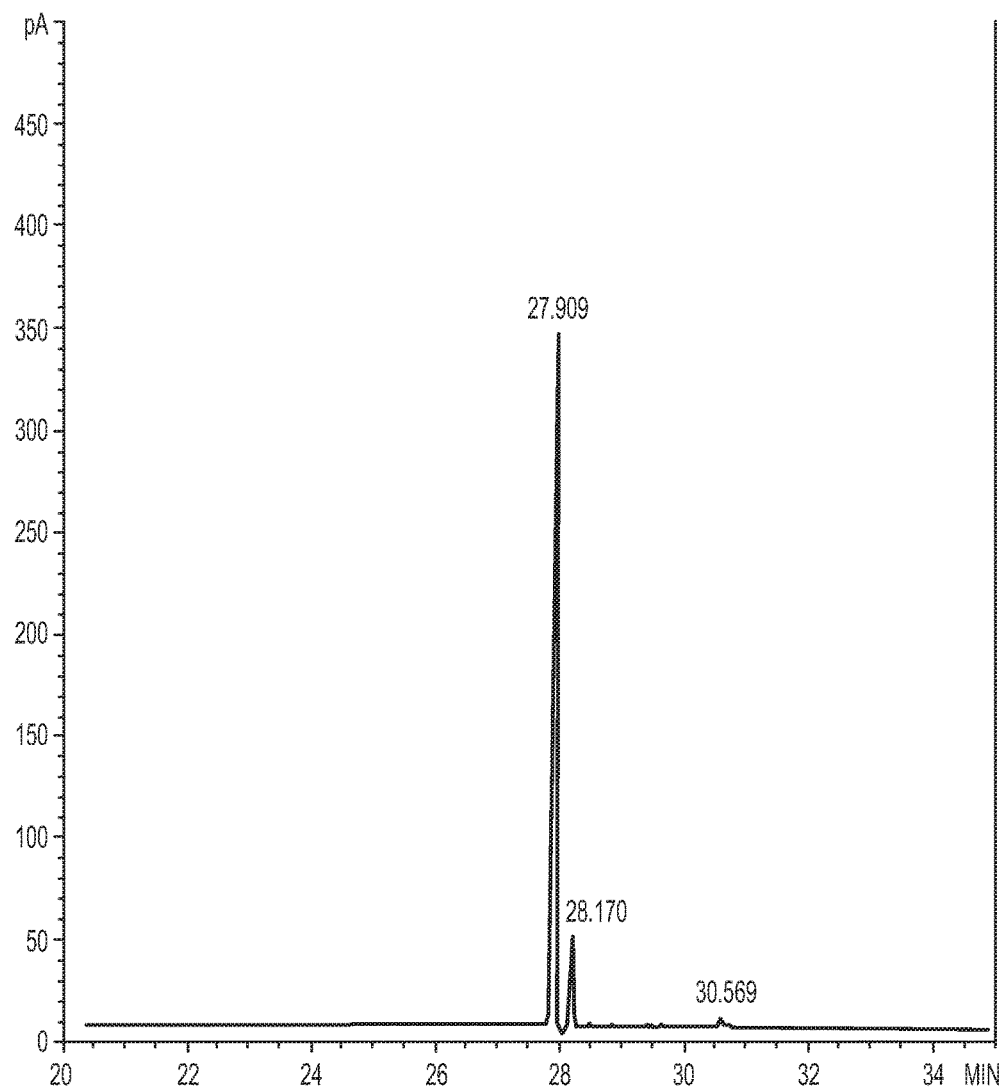
FIG. 2 shows a gas chromatograph of a composition (A-2) prepared in Preparation Example 2.

The resulting composition (A-2) was analyzed by gas chromatography under the analysis conditions described in Preparation Example 1. FIG. 2 shows a gas chromatograph of the composition (A-2). As shown in FIG. 2, peaks derived from the stereoisomers of the compound represented by Formula (1) were observed within the range of retention time of from 27.5 to 29.0 minutes. As shown in FIG. 2, the ratio of the area of the maximum peak within the range of retention time of from 27.6 to 28.0 minutes with respect to the total area of peaks within the range of retention time of from 27.5 to 29.0 minutes was 91%.

3. Preparation Example 3: Preparation of Composition (A-3)

A quantity of 3.65 g of mother liquor concentrate which had been obtained when filtering the composition (A-1) in the crystallization operation in the procedure of preparing the composition (A-1), was purified by silica gel column chromatography, to obtain 2.25 g of a composition (A-3).

Figure 3:
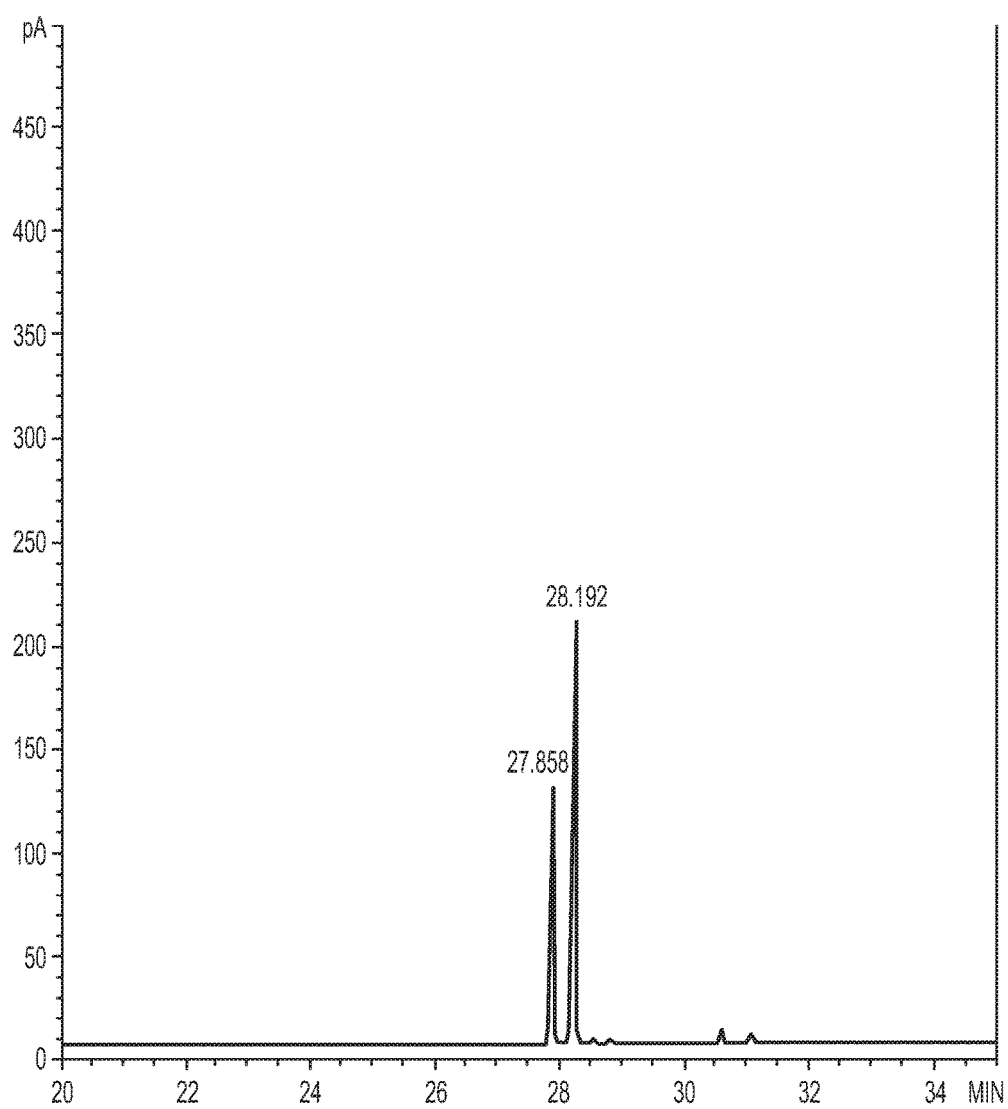
FIG. 3 shows a gas chromatograph of a composition (A-3) prepared in Preparation Example 3.

The resulting composition (A-3) was analyzed by gas chromatography under the analysis conditions described in Preparation Example 1. FIG. 3 shows a gas chromatograph of the composition (A-3). As shown in FIG. 3, peaks derived from the stereoisomers of the compound represented by Formula (1) were observed within the range of retention time of from 27.5 to 29.0 minutes. As shown in FIG. 3, the ratio of the area of the maximum peak within the range of retention time of from 27.6 to 28.0 minutes with respect to the total area of peaks within the range of retention time of from 27.5 to 29.0 minutes was 36%.

4. Preparation Example 4: Preparation of Composition (A-4)

Into a reaction vessel equipped with a thermometer, an agitator, a reflux tube and a dropping device, 4.3 g of 35% hydrogen peroxide and 0.30 g of $H_3PW_{12}O_{40}$ were charged, followed by stirring at 60° C. for 30 minutes. After cooling the resultant to 40° C., 36.2 g of the diolefin compound represented by the above described Formula (4), 0.11 g of cetylpyridinium chloride, and 252 g of chloroform were added thereto. Subsequently, 38.9 g of 35% hydrogen peroxide was added dropwise while stirring at 40° C., and a reaction was allowed proceed at 40° C. for six hours.

[Chem. 11]

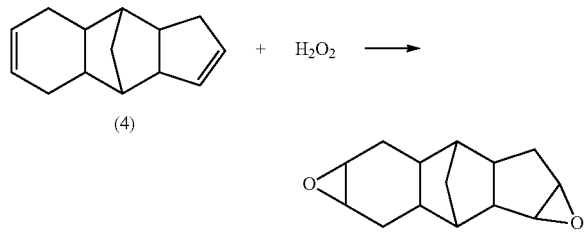

After the completion of the reaction, 180 g of chloroform was used to carry out a separation and extraction operation. The organic layer was washed with 120 mL of a 10% aqueous solution of sodium thiosulfate, 120 mL of a 10% aqueous solution of sodium carbonate, and 120 mL of pure water. After carrying out a dehydration operation with sodium sulfate, a rotary evaporator was used to remove the solvent contained therein by distillation. The resultant was then subjected to distillation at a pressure of 2 hPa and at a bottom temperature of from 180 to 200° C., to obtain 6.0 g of a composition (A-4), which is a composition of interest, at a bottom temperature 195° C.

Figure 4:
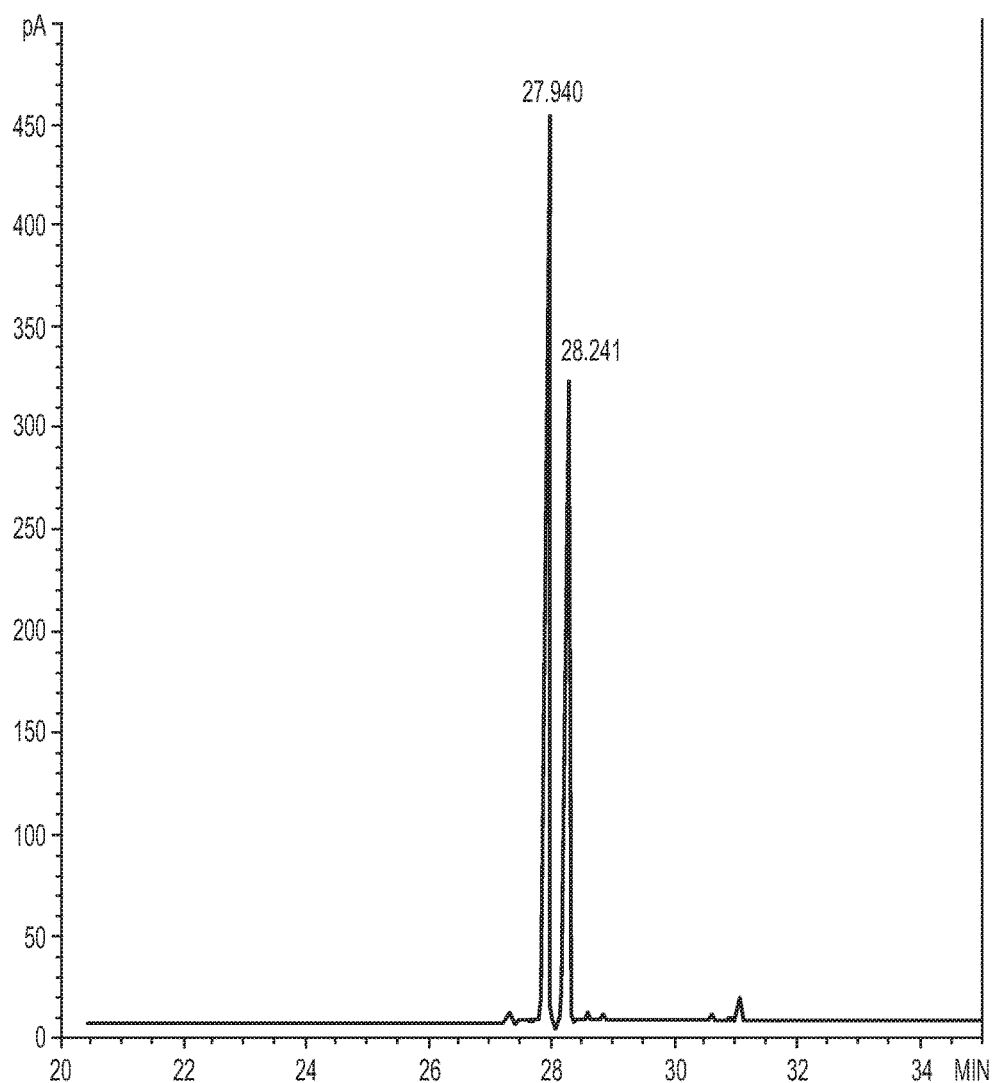
FIG. 4 shows a gas chromatograph of a composition (A-4) prepared in Preparation Example 4.

The resulting composition (A-4) was analyzed by gas chromatography under the analysis conditions described in Preparation Example 1. FIG. 4 shows a gas chromatograph of the composition (A-4). As shown in FIG. 4, peaks derived from the stereoisomers of the compound represented by Formula (1) were observed within the range of retention time of from 27.5 to 29.0 minutes. As shown in FIG. 4, the ratio of the area of the maximum peak within the range of retention time of from 27.6 to 28.0 minutes with respect to the total area of peaks within the range of retention time of from 27.5 to 29.0 minutes was 62%.

5. Example 1: Preparation of Curable Compositions Containing

Compositions (A-1 to A-4) and Evaluation Thereof (1) Example 1-1

Production of Curable Composition

The composition (A-2) obtained by the method described in Preparation Example 2 and a thermal cationic polymerization initiator were mixed to achieve the following composition, to obtain a curable composition.
<Composition of Curable Composition>

Composition (A-2) 100 parts by mass (the composition obtained by the method described in the Preparation Example 2)

Thermal cationic polymerization initiator 2 parts by mass (an aromatic sulfonium salt: 4-acetoxyphenyldimethylsulfonium hexafluoroantimonate, manufactured by Sanshin Chemical Industry Co., Ltd., trade name: SI-150L)

(2) Example 1-2

A curable composition was obtained in the same manner as in Example 1-1, except that the composition (A-1) (the composition obtained by the method described in the Preparation Example 1) was used instead of the composition (A-2).

(3) Example 1-3

A curable composition was obtained in the same manner as in Example 1-1, except that the composition (A-4) (the composition obtained by the method described in the Preparation Example 4) was used instead of the composition (A-2).

(4) Reference Example 1-1

A curable composition was obtained in the same manner as in Example 1-1, except that the composition (A-3) (the composition obtained by the method described in the Preparation Example 3) was used instead of the composition (A-2).
<Evaluation of Physical Properties>

The curable compositions obtained in the Examples and Reference Example were heated in a hot air circulating oven at 130° C. for one hour, at 150° C. for one hour, at 180° C. for two hours, and then at 220° C. for three hours, to obtain cured products.

The glass transition temperature of each of the thus obtained cured products was measured by increasing the temperature from 30 to 300° C. at a rate of 10° C./min, using a differential scanning calorimeter, DSC7020, manufactured by SII NanoTechnology Inc., and the thus measured value was taken as the heat resistance of the cured product. The glass transition temperature as used herein refers to a value measured in accordance with JIS K7121, based on "Midpoint Glass Transition Temperature: $T_{mg}$" described in the section of "Method for Measuring Transition Temperature of Plastics". The measurement results are summarized in Table 1.

TABLE 1

| | | Example 1-1 | Example 1-2 | Example 1-3 | Reference Example 1-1 |
|---|---|---|---|---|---|
| Composition of curable resin composition (parts by mass) | Composition (A-2) | 100 | | | |
| | Composition (A-1) | | 100 | | |
| | Composition (A-4) | | | 100 | |
| | Composition (A-3) | | | | 100 |
| | Thermal cationic polymerization initiator | 2 | 2 | 2 | 2 |
| Heat resistance (° C.) | | 250 | 248 | 245 | 241 |

6. Preparation Example 5: Preparation of Composition (A-5)

A quantity of 1.02 g of the composition (A-2) was dissolved in isopropyl alcohol at 60° C., and cooled to 25° C. to allow crystallization to occur, followed by collecting solids by filtration. The solids collected by filtration were washed with 5 mL of isopropyl alcohol, and then dried to obtain 0.500 g of a composition (A-5).

Figure 5:
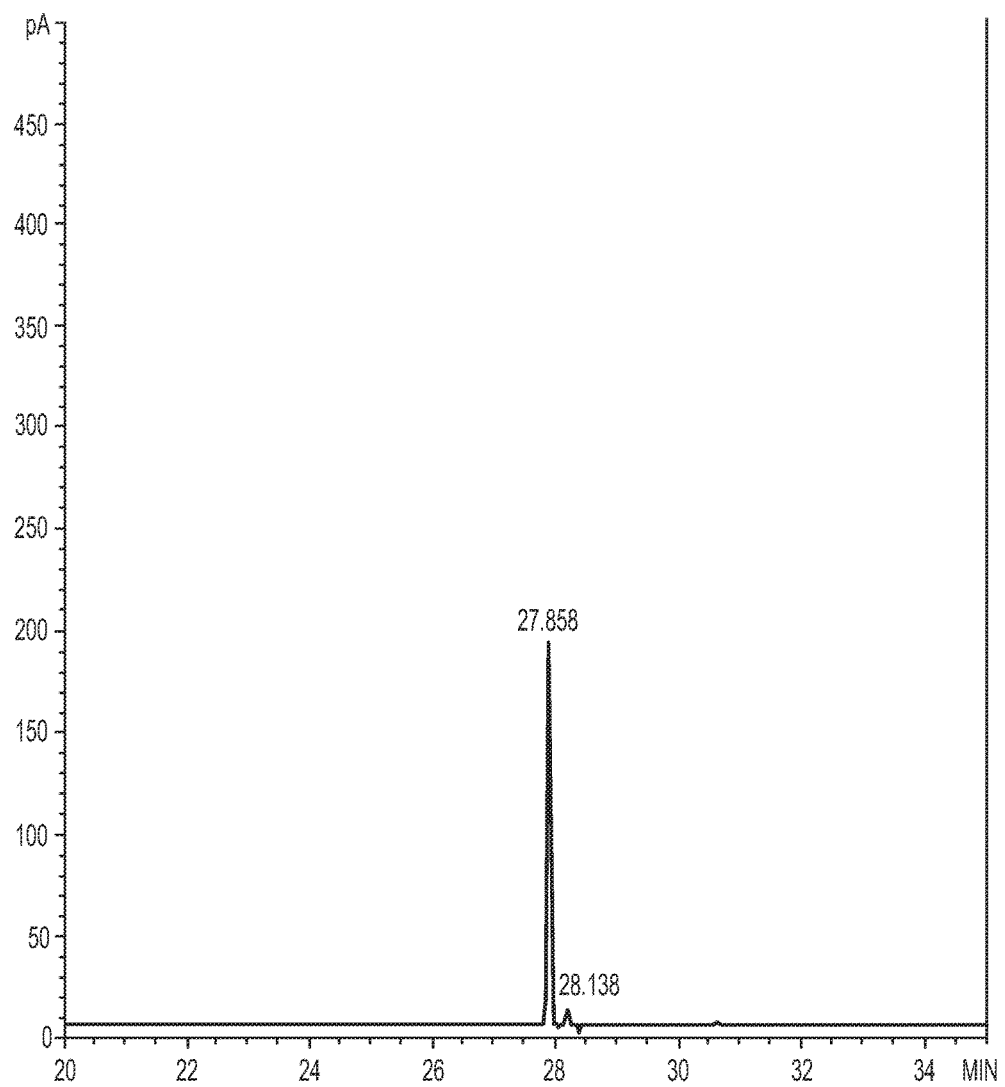
FIG. 5 shows a gas chromatograph of a composition (A-5) prepared in Preparation Example 5.

The resulting composition (A-5) was analyzed by gas chromatography under the analysis conditions described in Preparation Example 1. FIG. 5 shows a gas chromatograph of the composition (A-5). As shown in FIG. 5, peaks derived from the stereoisomers of the compound represented by Formula (1) were observed within the range of retention time of from 27.5 to 29.0 minutes. As shown in FIG. 5, the ratio of the area of the maximum peak within the range of retention time of from 27.6 to 28.0 minutes with respect to the total area of peaks within the range of retention time of from 27.5 to 29.0 minutes was 96%.

The stereoisomeric structure of the resulting composition (A-5) was identified by $^1$H-NMR and $^{13}$C-NMR.

Figure 6:
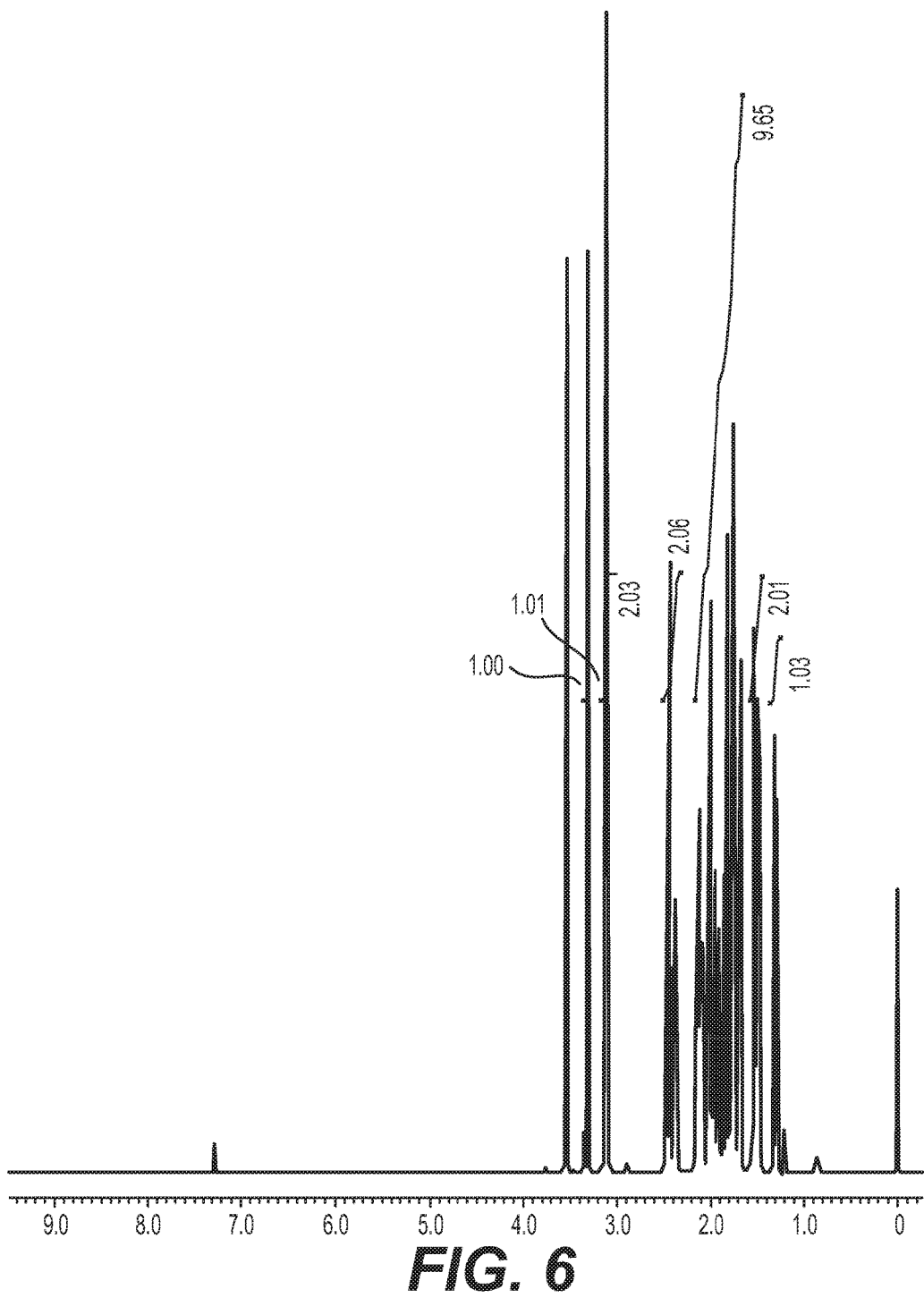
FIG. 6 is a chart showing $^1$H NMR peaks of the composition (A-5) prepared in Preparation Example 5.
Figure 7:
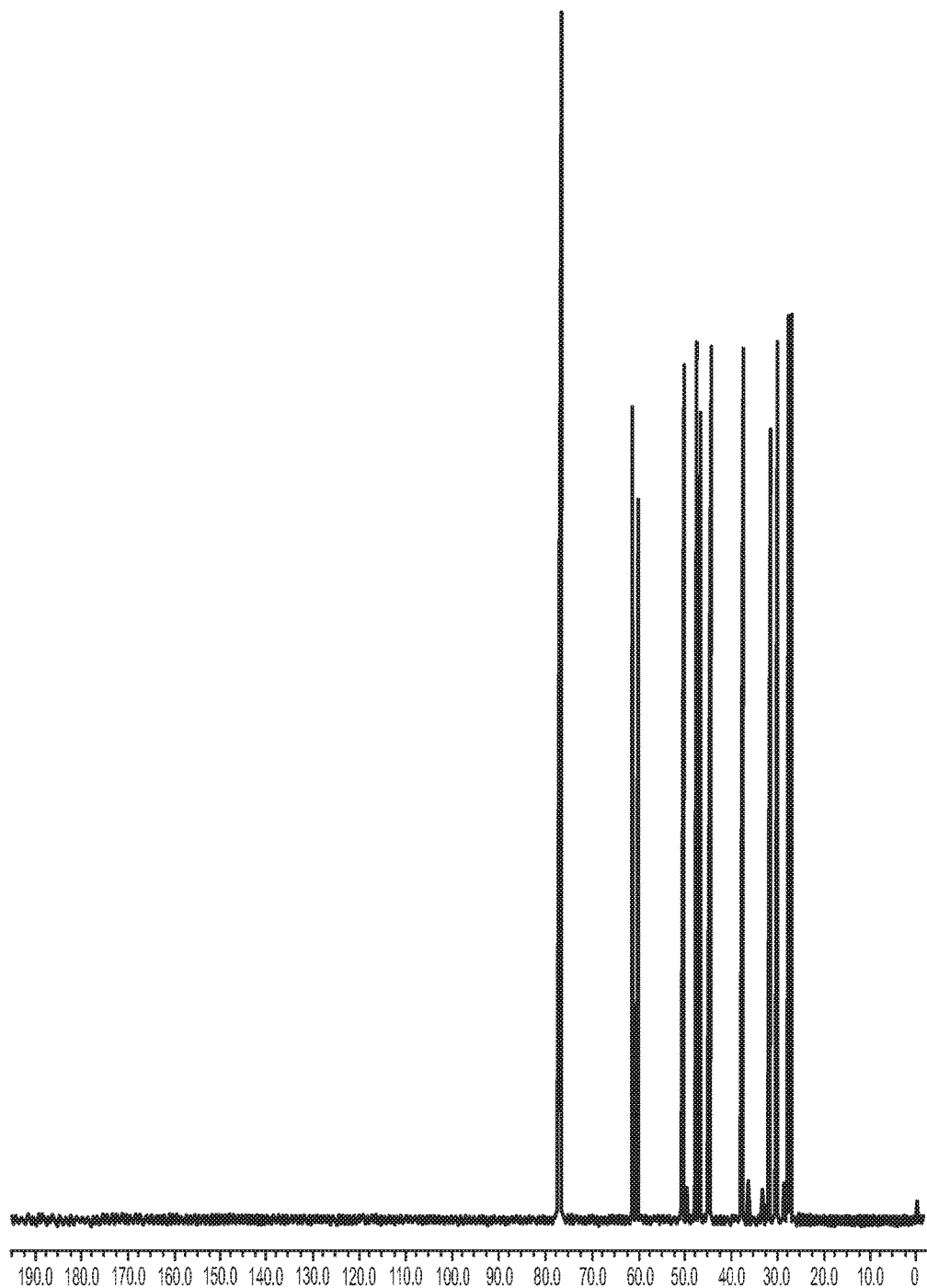
FIG. 7 is a chart showing $^{13}$C NMR peaks of the composition (A-5) prepared in Preparation Example 5.

A chart showing $^1$H NMR peaks of the composition (A-5) is shown in FIG. 6, and a chart showing $^{13}$C NMR peaks of the composition (A-5) is shown in FIG. 7. Based on the results of these NMR analyses and the above described chromatography analysis, it is thought that the mother nucleus structure of a compound represented by the maximum peak in the composition (A-5) has a steric configuration represented by the following Formula (5):

[Chem. 12]

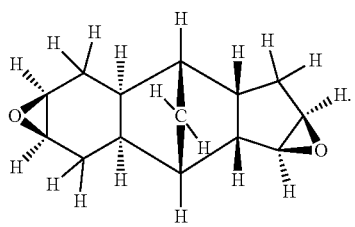

(5)

7. Preparation Example 6: Production of Monoepoxy Compound as Reactive Diluent

Production Example of Monoepoxy Compound

Into a reaction vessel equipped with a thermometer, an agitator, a reflux tube and a dropping device, 3,132 g of the diolefin compound represented by the following Formula (6), 3,132 g of toluene and sodium acetate were charged. To the reactor, 3,783 g of a 38% aqueous solution of peracetic acid was added dropwise over five hours, while stirring at −5° C. While continuing to stir the mixture at −5° C., a reaction was allowed to proceed for 17 hours.

Subsequently, a 10% aqueous solution of sodium sulfite was used to carry out a neutralization treatment, followed by a liquid separation operation. The resultant was then subjected to distillation at a pressure of 2 hPa and at a bottom temperature of from 130 to 140° C., to obtain 2,109 g of a colorless transparent liquid. In the $^{13}$C-NMR spectrum and the precise mass measurement by LC-MS, the [M+H]+ of the thus obtained liquid was determined to be 191.1439, which corresponds to the theoretical structure. Accordingly, it was confirmed that the resulting liquid was a monoepoxy compound of interest satisfying the following Formula (7). The viscosity of the resulting monoepoxy compound was measured using a Type E viscometer, to be 11.0 mPa·s.

[Chem. 13]

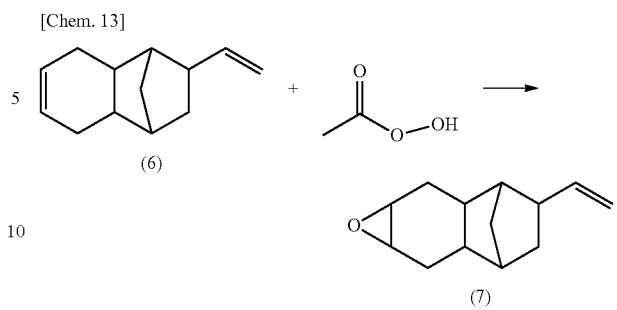

The invention claimed is:

1. A composition comprising at least one or more stereoisomers of a compound represented by the following Formula (1):

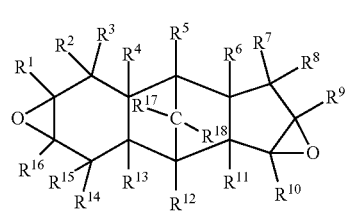

(1)

(wherein $R^1$ to $R^{18}$ are each independently selected from the group consisting of a hydrogen atom, an alkyl group and an alkoxy group)
wherein, in a gas chromatogram obtained by analyzing the composition by gas chromatography under the following analysis conditions, the ratio of the area of the maximum peak with respect to the total area of peaks derived from the stereoisomers is 60% or more, wherein the maximum peak is present within the range of retention time of from 27.6 to 28.0 minutes, and
wherein the analysis conditions are as follows:
column: HP-1 (manufactured by Agilent Technologies Inc.), length: 60.0 m, inner diameter: 250 μm, film thickness: 0.25 μm;
liquid phase: 100% dimethylpolysiloxane;
carrier gas: N$_2$;
flow velocity: 1.3 mL/min;
sample inlet temperature: 140° C.;
detector temperature: 250° C.;
sample injection volume: 0.2 μL; and
temperature increase conditions: 80° C. (3 min), 80 to 150° C. (10° C./min), 150 to 250° C. (5° C./min), 250° C. (20 min).

2. A composition comprising at least one or more stereoisomers of a compound represented by the following Formula (1):

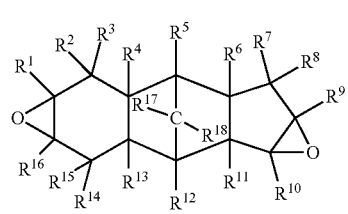

(1)

(wherein $R^1$ to $R^{18}$ are each independently selected from the group consisting of a hydrogen atom, an alkyl group and an alkoxy group)

wherein, in a gas chromatogram obtained by analyzing the composition by gas chromatography under the following analysis conditions, the ratio of the area of the maximum peak within the range of retention time of from 27.6 to 28.0 minutes with respect to the total area of peaks within the range of retention time of from 27.5 to 29.0 minutes is 60% or more, and wherein the analysis conditions are as follows:

column: HP-1 (manufactured by Agilent Technologies Inc.), length: 60.0 m, inner diameter: 250 µm, film thickness: 0.25 µm;
liquid phase: 100% dimethylpolysiloxane;
carrier gas: $N_2$;
flow velocity: 1.3 mL/min;
sample inlet temperature: 140° C.;
detector temperature: 250° C.;
sample injection volume: 0.2 µL; and
temperature increase conditions: 80° C. (3 min), 80 to 150° C. (10° C./min), 150 to 250° C. (5° C./min), 250° C. (20 min).

3. The composition according to claim 1, wherein the compound represented by the Formula (1) is a reaction product of a compound represented by the following Formula (2):

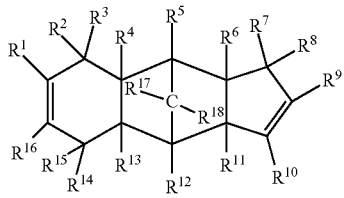

(2)

(wherein $R^1$ to $R^{18}$ are each independently selected from the group consisting of a hydrogen atom, an alkyl group and an alkoxy group)
with a peracid.

4. The composition according to claim 1, wherein the maximum peak is the first peak among the peaks derived from the stereoisomers.

5. The composition according to claim 1, wherein the maximum peak is the first peak appearing after a retention time of 27.5 minutes, among the peaks within the range of retention time of from 27.5 to 29.0 minutes.

6. The composition according to claim 1, wherein the $R^1$ to $R^{18}$ are all hydrogen atoms.

7. The composition according to claim 1, wherein the stereoisomer corresponding to the maximum peak is represented by the following Formula (3):

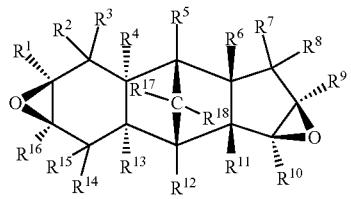

(3)

(wherein $R^1$ to $R^{18}$ are each independently selected from the group consisting of a hydrogen atom, an alkyl group and an alkoxy group).

8. An epoxy compound represented by the following Formula (3):

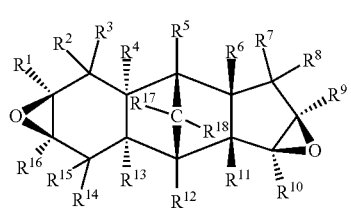

(3)

(wherein $R^1$ to $R^{18}$ are each independently selected from the group consisting of a hydrogen atom, an alkyl group and an alkoxy group), wherein, in a gas chromatogram obtained by analyzing the composition by gas chromatography under the following analysis conditions, the ratio of the area of the maximum peak with respect to the total area of peaks derived from the stereoisomers is 60% or more, wherein the maximum peak is present within the range of retention time of from 27.6 to 28.0 minutes, and wherein the analysis conditions are as follows:

column: HP-1 (manufactured by Agilent Technologies Inc.), length: 60.0 m, inner diameter: 250 µm, film thickness: 0.25 µm;
liquid phase: 100% dimethylpolysiloxane;
carrier gas: $N_2$;
flow velocity: 1.3 mL/min;
sample inlet temperature: 140° C.;
detector temperature: 250° C.;
sample injection volume: 0.2 µL; and
temperature increase conditions: 80° C. (3 min), 80 to 150° C. (10° C./min), 150 to 250° C. (5° C./min), 250° C. (20 min).

9. A curable composition comprising:
the epoxy composition according to claim 1 or an epoxy compound represented by the following Formula (3):

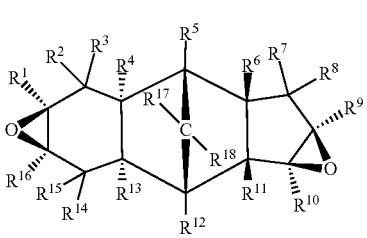

(3)

(wherein $R^1$ to $R^{18}$ are each independently selected from the group consisting of a hydrogen atom, an alkyl group and an alkoxy group), wherein, in a gas chromatogram obtained by analyzing the composition by gas chromatography under the following analysis conditions, the ratio of the area of the maximum peak with respect to the total area of peaks derived from the stereoisomers is 60% or more, wherein the maximum peak is present within the range of retention time of from 27.6 to 28.0 minutes, and wherein the analysis conditions are as follows:
column: HP-1 (manufactured by Agilent Technologies Inc.), length: 60.0 m, inner diameter: 250 μm, film thickness: 0.25 μm;
liquid phase: 100% dimethylpolysiloxane;
carrier gas: $N_2$;
flow velocity: 1.3 mL/min;
sample inlet temperature: 140° C.;
detector temperature: 250° C.;
sample injection volume: 0.2 μL; and
temperature increase conditions: 80° C. (3 min), 80 to 150° C. (10° C./min), 150 to 250° C. (5° C./min), 250° C. (20 min); and
    one selected from the group consisting of: a thermal cationic polymerization initiator, an acid anhydride-based curing agent and a curing accelerator, and a photo-cationic polymerization initiator.

10. The curable composition according to claim 9, further comprising one kind, or two or more kinds selected from the group consisting of an epoxy compound other than the compound represented by the Formula (1), an oxetane compound and a vinyl ether.

11. The curable composition according to claim 9, wherein the thermal cationic polymerization initiator is selected from the group consisting of aromatic sulfonium salt-based thermal cationic polymerization initiators, aromatic iodonium salt-based thermal cationic polymerization initiators and aluminum complex-based thermal cationic polymerization initiators.

12. The curable composition according to claim 11, wherein the thermal cationic polymerization initiator is an aromatic sulfonium salt-based thermal cationic polymerization initiator.

13. The curable composition according to claim 10, wherein, in cases where the curable composition does not comprise any of the epoxy compound other than the compound represented by the Formula (1), the oxetane compound and the vinyl ether, the content of the thermal cationic polymerization initiator is from 0.1 to 15 parts by mass with respect to 100 parts by mass of the composition contained in the curable composition; and in cases where the curable composition comprises one kind, or two or more kinds selected from the group consisting of the epoxy compound other than the compound represented by the Formula (1), the oxetane compound and the vinyl ether, the content of the thermal cationic polymerization initiator is from 0.1 to 15 parts by mass with respect to 100 parts by mass of the total amount of the epoxy composition, the epoxy compound other than the compound represented by the Formula (1), the oxetane compound and the vinyl ether, which are contained in the curable composition.

14. The curable composition according to claim 10, wherein, in cases where the curable composition does not comprise the epoxy compound other than the compound represented by the Formula (1), the content of the acid anhydride-based curing agent is from 0.6 to 1.2 equivalents with respect to one epoxy equivalent of the composition contained in the curable composition; and in cases where the curable composition comprises the epoxy compound other than the compound represented by the Formula (1), the content of the acid anhydride-based curing agent is from 0.6 to 1.2 equivalents with respect to one epoxy equivalent of a mixture of epoxy compounds composed of the composition and the epoxy compound other than the compound represented by the Formula (1), which are contained in the curable composition.

15. The curable composition according to claim 10, wherein, in cases where the curable composition does not comprise the epoxy compound other than the compound represented by the Formula (1), the content of the curing accelerator is from 0.1 to 10 parts by mass with respect to 100 parts by mass of the composition contained in the curable composition; and in cases where the curable composition comprises the epoxy compound other than the compound represented by the Formula (1), the content of the curing accelerator is from 0.1 to 10 parts by mass with respect to 100 parts by mass of the total amount of the composition and the epoxy compound other than the compound represented by the Formula (1), which are contained in the curable composition.

16. The curable composition according to claim 9, wherein the curing accelerator is an imidazole-based curing accelerator.

17. The curable composition according to claim 11, wherein the content of the composition is from 10 to 99% by mass.

18. The curable composition according to claim 9, wherein the photo-cationic polymerization initiator is an aromatic sulfonium salt-based photo-cationic polymerization initiator.

19. The curable composition according to claim 10, wherein, in cases where the curable composition does not comprise any of the epoxy compound other than the compound represented by the Formula (1), the oxetane compound and the vinyl ether, the content of the photo-cationic polymerization initiator is from 0.1 to 20 parts by mass with respect to 100 parts by mass of the composition contained in the curable composition; and in cases where the curable composition comprises one kind, or two or more kinds selected from the group consisting of the epoxy compound other than the compound represented by the Formula (1), the oxetane compound and the vinyl ether, the content of the photo-cationic polymerization initiator is from 0.1 to 20 parts by mass with respect to 100 parts by mass of the total amount of the composition, the epoxy compound other than the compound represented by the Formula (1), the oxetane compound and the vinyl ether, which are contained in the curable composition.

20. The curable composition according to claim 18, wherein the content of the composition is from 1 to 50% by mass.

21. The curable composition according to claim 10, wherein the epoxy compound other than the compound represented by the Formula (1) is selected from the group consisting of glycidyl ether-type epoxides, glycidyl ester-type epoxides and alicyclic epoxides.

22. A method of producing a cured product, the method comprising the step of curing the curable composition according claim 9.

23. A cured product from the curable composition according to claim 9.

\* \* \* \* \*